(12) United States Patent
Urban et al.

(10) Patent No.: US 10,830,639 B2
(45) Date of Patent: Nov. 10, 2020

(54) DEVICES, METHODS, AND SYSTEMS RELATING TO SUPER RESOLUTION IMAGING

(71) Applicant: Northwestern University, Evanston, IL (US)

(72) Inventors: Ben Urban, Evanston, IL (US); Hao F. Zhang, Deerfield, IL (US); Cheng Sun, Wilmette, IL (US); Biqin Dong, Evanston, IL (US)

(73) Assignee: Northwestern University, Evanston, IL (US)

( * ) Notice: Subject to any disclaimer, the term of this patent is extended or adjusted under 35 U.S.C. 154(b) by 32 days.

(21) Appl. No.: 15/514,084

(22) PCT Filed: Sep. 25, 2015

(86) PCT No.: PCT/US2015/052388
§ 371 (c)(1),
(2) Date: Mar. 24, 2017

(87) PCT Pub. No.: WO2016/049544
PCT Pub. Date: Mar. 31, 2016

(65) Prior Publication Data
US 2017/0307440 A1    Oct. 26, 2017

Related U.S. Application Data

(60) Provisional application No. 62/055,398, filed on Sep. 25, 2014.

(51) Int. Cl.
*G01N 21/64*    (2006.01)
*G01J 1/42*    (2006.01)
(Continued)

(52) U.S. Cl.
CPC ........ *G01J 1/4228* (2013.01); *G01N 21/6458* (2013.01); *G01N 21/65* (2013.01);
(Continued)

(58) Field of Classification Search
CPC .... G01N 21/6428; G01N 21/65; G01N 21/84; G01N 21/483; G01N 33/483; G02B 21/0064; G02B 21/367; G02B 21/58
See application file for complete search history.

(56) References Cited

U.S. PATENT DOCUMENTS

| 4,650,321 A | 3/1987 | Thompson |
| 5,981,179 A | 11/1999 | Lorinez et al. |

(Continued)

FOREIGN PATENT DOCUMENTS

| WO | WO 2008/091296 | 7/2008 |
| WO | 2016049544 | 3/2016 |

OTHER PUBLICATIONS

International Bureau, "International Preliminary Report on Patentability", issued in connection with PCT patent application No. PCT/US2015/052388, dated Mar. 28, 2017, 8 pages.

(Continued)

*Primary Examiner* — David P Porta
*Assistant Examiner* — Mamadou Faye
(74) *Attorney, Agent, or Firm* — Leydig, Voit & Mayer, Ltd.

(57) ABSTRACT

Certain examples disclose systems and methods for imaging a target. An example method includes: a) activating a subset of light-emitting molecules in a wide field area of a target using an excitation light; b) capturing one or more images of the light emitted from the subset of the molecules illuminated with the excitation light; c) localizing one or more activated light emitting molecules using one or more single molecule microscopic methods to obtain localization infor- (Continued)

mation; d) simultaneously capturing spectral information for the same localized activated light emitting molecules using one or more spectroscopic methods; e) resolving one or more non-diffraction limited images of the area of the target using a combination of the localization and spectral information for the localized activated light emitting molecules; and f) displaying the one or more non-diffraction limited images.

33 Claims, 22 Drawing Sheets

(51) Int. Cl.
    *G02B 21/36*     (2006.01)
    *G01N 21/65*     (2006.01)
    *G02B 21/00*     (2006.01)
    *G02B 27/58*     (2006.01)
    *G01N 21/84*     (2006.01)
    *G01N 33/483*     (2006.01)

(52) U.S. Cl.
    CPC ........... *G01N 21/84* (2013.01); *G01N 33/483* (2013.01); *G02B 21/008* (2013.01); *G02B 21/0032* (2013.01); *G02B 21/0064* (2013.01); *G02B 21/0076* (2013.01); *G02B 21/367* (2013.01); *G02B 27/58* (2013.01)

(56) References Cited

U.S. PATENT DOCUMENTS

| | | | |
|---|---|---|---|
| 5,998,796 | A | 12/1999 | Liu et al. |
| 8,599,388 | B1 | 12/2013 | van Dijk et al. |
| 9,435,992 | B2 | 9/2016 | Kleppe et al. |
| 9,690,086 | B2 | 6/2017 | Foelling |
| 9,784,666 | B2 | 10/2017 | Mai et al. |
| 2004/0023415 | A1 | 2/2004 | Sokolov et al. |
| 2005/0237493 | A1 | 10/2005 | Tajiri |
| 2007/0178067 | A1* | 8/2007 | Maier ............ G01N 21/65 424/93.2 |
| 2011/0021369 | A1 | 1/2011 | Mhlanga et al. |
| 2011/0081653 | A1* | 4/2011 | Hell ............ G01N 21/6428 435/6.19 |
| 2013/0027518 | A1* | 1/2013 | MacKay ............ G02B 21/26 348/46 |
| 2013/0147916 | A1* | 6/2013 | Bennett ............ G01B 11/24 348/46 |
| 2013/0228704 | A1* | 9/2013 | Kalkbrenner ........ G01N 21/64 250/459.1 |
| 2013/0314526 | A1 | 11/2013 | Yasuda et al. |
| 2014/0176678 | A1* | 6/2014 | Novikau ............ G02B 21/16 348/46 |
| 2014/0333750 | A1* | 11/2014 | Zhuang ............ G02B 21/367 348/79 |
| 2014/0340482 | A1 | 11/2014 | Kanarowski |
| 2015/0192510 | A1* | 7/2015 | Piestun ............ G01B 11/002 702/151 |
| 2018/0088048 | A1 | 3/2018 | Dong et al. |

OTHER PUBLICATIONS

International Searching Authority, "International Search Report and Written Opinion", issued in connection with PCT patent application No. PCT/US15/52388, dated Jan. 5, 2016, 13 pages.
Matsuzaki et al, "Superresolution vibrational imaging by simultanous detecting of Raman and hyper-Raman scattering", Optics Letters, Optical Society of America, US, vol. 36, No. 13, Jul. 1, 2011, 3 pages.
Ambrose et al. (1991) "Fluorescence Spectroscopy and Spectral Diffusion of Single Impurity Molecules in a Crystal," Letters to Nature 349: 225-227.
Anders (1981) "DNA Fluorescence at Room-Temperature Excited by Means of a Dye-Laser," Chemical Physics Letters 81(2): 270-272.
Axelrod (1979) "Carbocyanine Dye Orientation in Red-Cell Membrane Studied by Microscopic Fluorescence Polarization," Biophysical Journal 26(3): 557-573.
Backer et al. (Jun. 2016) "Enhanced DNA imaging using super-resolution microscopy and simultaneous single-molecule orientation measurements," Optica Society of America, 3(6): 659-666.
Balzarotti et al. (Feb. 2017) "Nanometer resolution imaging and tracking of fluorescent molecules with minimal photon fluxes," Science 355: 606-612.
Bancaud et al. (2012) "A fractal model for nuclear organization: current evidence and biological implications," Nucleic Acids Research 40(18): 8783-8792.
Barbatti et al. (Month unavailable, 2015) "Photoinduced Phenomena in Nucleic Acids I", Topics in Current Chemistry, Springer 355: 365 pages.
Basche et al. (2007) "Single-Molecule Optical Detection, Imaging and Spectroscopy" VCH Verlagsgesellschaft mbH, 15 pages.
Betzig et al. (2006) "Imaging intracellular fluorescent proteins at nanometer resolution," Science 313: 1642-1645.
Blumberger (Oct. 2015) "Recent Advances in the Theory and Molecular Simulation of Biological Electron Transfer Reactions," Chemical Reviews 115: 11191-11238.
Boettiger et al. (Jan. 2016) "Super-resolution imaging reveals distinct chromatin folding for different epigenetic states," Nature 529: 418-422.
Bohrmann et al. (1993) "Concentration evaluation of chromatin in unstained resin-embedded sections by means of low-dose ratio-contrast imaging in STEM," Ultramicroscopy 49: 235-251.
Buchvarov et al. (2007) "Electronic energy delocalization and dissipation in single- and double-stranded DNA," Proceedings of the National Academy of Sciences of the United States of America 104(12): 4794-4797.
Burzykowski et al. (2003) "Analysis of photon count data from single-molecule fluorescence experiments," Chemical Physics 288: 291-307.
Chen et al. (2001) "Polarization spectroscopy of single CdSe quantum rods" Physical Review B, 64(24): 245304-1-245304-4.
Chen et al. (Oct. 2014) "Lattice light-sheet microscopy: Imaging molecules to embryos at high spatiotemporal resolution", Science 346(6208): 1257998-1-1257998-12.
Cruz et al. (Feb. 2016) "Quantitative nanoscale imaging of orientational order in biological filaments by polarized superresolution microscopy." Proceedings of the National Academy of Sciences of the United States of America 113(7): E820-E828.
Daban (2003) "High concentration of DNA in condensed chromatin," Biochem. Cell Biol 81: 91-99.
Dempsey et al. (2011) "Evaluation of fluorophores for optimal performance in localization-based superresolution imaging," Nature Methods 8(12): 1027-1036.
Dong et al. (Jul. 2016) "Super-resolution spectroscopic microscopy via photon localization", Nature Communications 7, 12290: 1-8.
Dong et al. (Aug. 2016) "Superresolution intrinsic fluorescence imaging of chromatin utilizing native, unmodified nucleic acids for contrast," Proceedings of the National Academy of Science 113(35): 9716-9721.
Dong et al. (Apr. 2017) "Stochastic fluorescence switching of nucleic acids under visible light illumination," Optics Express 25(7): 7929-7944.
Dunn et al. (2011) "A practical guide to evaluating colocalization in biological microscopy," American Journal of Physiology-Cell Physiology 300: C723-C742.
Ellis et al. (2003) "Cell biology—Join the crowd," Nature, 425: 27-28.
Fölling et al. (2008) "Fluorescence nanoscopy by ground-state depletion and single-molecule return," Nature Methods 5(11): 943-945.
Gao et al. (2012) "Snapshot hyperspectral retinal camera with the Image Mapping Spectrometer (IMS)" Biomedical Optics Express 3(1): 48-54.

(56) References Cited

OTHER PUBLICATIONS

Gould et al. (2008) "Nanoscale imaging of molecular positions and anisotropies", Nature Methods 5(12): 1027-1030.
Hedegaard et al. (2011) "Spectral unmixing and clustering algorithms for assessment of single cells by Raman microscopic imaging," Theoretical Chemistry Accounts 130: 1249-1260.
Hiraoka et al. (2002) "Multispectral imaging fluorescence microscopy for living cells", Cell Structure and Function 27(5): 367-374.
Huang et al. (2008) "Three-dimensional super-resolution imaging by stochastic optical reconstruction microscopy," Science 319:810-813.
Hu et al (Jul. 2015) "Deep convolutional neural networks for hyperspectral image classification," Journal of Sensors, 2015: 1-12.
Jing et al. (2011) "Chemical Tags for Labeling Proteins Inside Living Cells," Accounts of Chemical Research 44(9):784-792.
Johnson et al. (2007) "Snapshot hyperspectral imaging in ophthalmology", Journal of Biomedical Optics 12(1): 014036-1-014036-7.
Jones et al. (2011) "Fast, three-dimensional super-resolution imaging of live cells," Nature Methods 8(6): 499-505.
Juette et al. (Apr. 2016) "Single-molecule imaging of non-equilibrium molecular ensembles on the millisecond timescale" Nature Methods 13(4): 341-344.
Khoobehi (publicly available Dec. 2013) "A new snapshot hyperspectral imaging system to image optic nerve head tissue", Acta Ophthalmologica 92(3): e241, 1pp. (published May 2014).
Klar et al. (2000) "Fluorescence microscopy with diffraction resolution barrier broken by stimulated emission," PNAS 97(15): 8206-8210.
Kundukad et al. (Oct. 2014) "Effect of YOYO-1 on the mechanical properties of DNA," Soft Matter 10: 9721-9728.
Larsson et al. (1994) "Characterization of the Binding of the Fluorescent Dyes YO and YOYO to DNA by Polarized-Light Spectroscopy," Journal of the American Chemical Society 116(19): 8459-8465.
Lecun et al. (1998) "Gradient-based learning Applied to Document Recognition," Proceedings of the IEEE 86(11): 2278-2324.
Le Gros et al. (2005) "X-ray tomography of whole cells," Current opinion in structural biology 15: 593-600.
Lelek et al. (2012) "Superresolution imaging of HIV in infected cells with FlAsH-PALM," PNAS 109(22): 8564-8569.
Levenson et al. (2006) "Multispectral Imaging in Biology and Medicine: Slices of Life", Cytometry Part A 69a(8): 748-758.
Levi et al. (2005) "Chromatin Dynamics in Interphase Cells Revealed by Tracking in a Two-Photon Excitation Microscope," Biophysical Journal 89: 4275-4285.
Lu et al. (1997) "Single-molecule spectral fluctuations at room temperature," Letters to Nature 385: 143-146.
Macqueen (1967) "Some methods for classification and analysis of multivariate observations," in Proceedings of the fifth Berkeley symposium on mathematical statistics and probability (Oakland, CA, USA.): 281-297.
Manley et al. (2008) "High-density mapping of single-molecule trajectories with photoactivated localization microscopy," Nature Methods 5(2): 155-157.
Min et al. (2011) "Coherent Nonlinear Optical Imaging: Beyond Fluorescence Microscopy," Annual Review of Physical Chemistry 62: 507-530.
Mlodzianoski et al. (Mar. 2016) "Super-Resolution Imaging of Molecular Emission Spectra and Single Molecule Spectral Fluctuations" Plos One 11(3): 1-12.
Moerner (2007) "Single-molecule chemistry and biology special feature: New directions in single-molecule imaging and analysis" Proceedings of the National Academy of Sciences of the United States of America 104(39): 12596-12602.
Ovesny et al. (Apr. 2014) "ThunderSTORM: a comprehensive ImageJ plug-in for PALM and STORM data analysis and super-resolution imaging," Bioinformatics 30(16): 2389-2390.
Pearson (1901) "On lines and planes of closest fit to systems of point in space," Philosophical Magazine 2: 559-572.
Pfeiffer et al. (2000) "High-pressure freezing Provides New Information on Human Epidermis: Simultaneous Protein Antigen and Lamellar Lipid Structure Preservation. Study on Human Epidermis by Cryoimmobilization," Journal of Investigative Dermatology 114(5): 1030-1038.
Plessow et al. (2000) "Intrinsic time-and wavelength-resolved fluorescence of oligonucleotides: A systematic investigation using a novel picosecond laser approach," J. Phys. Chem. B 104: 3695-3704.
Razin et al. (Feb. 2014) "Chromatin without the 30-nm fiber Constrained disorder instead of hierarchical folding," Epigenetics 9(5): 653-657.
Rostaing et al. (2004) "Preservation of immunoreactivity and Fine Structure of Adult C. elegans Tissues Using High-pressure freezing," Journal of Histochemistry & Cytochemistry, 52(1): 1-12.
Roy et al. (Feb. 2015) "Nanocytological Field Carcinogenesis Detection to Mitigate Overdiagnosis of Prostate Cancer: A Proof of Concept Study," Plos One 10(2): 1-10.
Rust et al. (2006) "Sub-diffraction-limit imaging by stochastic optical reconstruction microscopy (STORM)," Nature Methods 3(10): 793-795.
Schmied et al. (May 2014) "DNA origami-based standards for quantitative fluorescence microscopy," Nature Protocols 9(6): 1367-1391.
Takaya et al. (2008) "UV excitation of single DNA and RNA strands produces high yields of exciplex states between two stacked bases," PNAS 105(30): 10285-10290.
Tremethick (2007) "Higher-order structures of Chromatin: The elusive 30 nm Fiber," Cell 128: 651-654.
Urban et al. (Jun. 2016) "Subsurface Super-resolution Imaging of Unstained Polymer Nanostructures," Scientific Reports 6, 28156: 1-9.
U.S. Office Action, dated Mar. 29, 2019, corresponding to U.S. Appl. No. 15/584,018, corresponding to the present application, 39 pp.
Van Driel et al. (2009) "Tools for correlative cryo-fluorescence microscopy and cryo-electron tomography applied to whole mitochondria in human endothelial cells," European Journal of Cell Biology 88: 669-684.
Vaya et al. (2010) "Fluorescence of Natural DNA: From the Femtosecond to the Nanosecond Time Scales," J. Am. Chem. Soc. 132(34):11834-11835.
Vincent et al. (2008) "Application of Optical Coherence Tomography for Monitoring Changes in Cervicovaginal Epithelial Morphology in Macaques:Potential for Assessment of Microbicide Safety" Sexually Transmitted Diseases 35(3): 269-275.
Vincent et al. (2009) "High Resolution Imaging of Epithelial Injury in then Sheep Cervicovaginal Tract: A Promising Model for Testing Safety of Candidate Microbicides", Sexually Transmitted Diseases 36(5): 312-318.
Walker (2006) "Quantification of immunohistochemistry—issues concerning methods, utility and semiquantitative assessment I", Histopathology 49: 406-410.
Ward (1963) "Hierarchical grouping to optimize an objective function," Journal of the American statistical association 58(301): 236-244.
Watanabe et al (2013) "Wide-area scanner for high-speed atomic force microscopy," Review of Scientific Instruments 84: 053702-1-053702-10.
Yeung (1999) "Study of single cells by using capillary electrophoresis and native flourescene detection," Journal of Chromatography A 830: 243-262.
Yokota et al. (1999) "Spin-stretching of DNA and Protein Molecules for Detection by Fluorescence and Atomic Force Microscopy," Analytical Chemistry 71: 4418-4422.
Yushchenko et al. (2012) "Tailoring Fluorescent Labels for Far-Field Nanoscopy", Springer 14: 159-188.
Zhang et al. (publicly available Aug. 2015) "Ultrahigh-throughput single-molecule spectroscopy and spectrally resolved super-resolution microscopy" Nature Methods 12(10): 935-938 (published Oct. 2015).
U.S. Office Action, dated Dec. 4, 2019, corresponding to U.S. Appl. No. 15/584,018, 26 pp.

(56) References Cited

OTHER PUBLICATIONS

Alizadeh et al. (2000) "Distinct types of diffuse large B-cell lymphoma identified by gene expression profiling," Nature 403: 503-511.
Ash et al. (1972) "Super-resolution aperture scanning microscope," Nature 237: 510-512.
Audic et al. (1997) "The Significance of Digital Gene Expression Profiles," Genomic Res. 7: 986-995.
Bates et al. (2010) "Sub-diffraction-limit imaging with stochastic optical reconstruction microscopy," In: Single Molecule Spectroscopy in Chemistry, Physics and Biology, Springer, pp. 399-415.
Brenner et al. (2000) "Gene expression analysis by massively parallel signature sequencing (MPSS) on microbead arrays," Nature Biotechnology 18: 630-634.
Brenner et al. (2000) "In vitro cloning of complex mixtures of DNA on microbeads: Physical separation of differentially expressed cDNAs," Proc. Natl. Acad. Sci. 97(4): 1665-1670.
Chee (1991) "Enzymatic multiplex DNA sequencing," Nucleic Acids Research 19(12): 3301-3305.
Chee et al. (1996) "Accessing Genetic Information with High-Density DNA Arrays," Science 274(5287): 610-614.
Church et al. (1988) "Multiplex DNA sequencing," Science 240(4849): 185-188.
Collins et al. (1998) "New Goals for the U.S. Human Genome Project: 1998-2003," Science 282(5389): 682-689.
De Clerck et al. (1994) "Use of fluorescent dyes in the determination of adherence of human leucocytes to endothelial cells and the effect of fluorochromes on cellular function," Journal of immunological methods 172: 115-124.
De Primo et al. (2003) "Expression profiling of blood samples from an SU5416 Phase III metastatic colorectal cancer clinical trial: a novel strategy for biomarker identification," BMC Cancer 3(3): 12 pp.
De Saizieu et al. (1998) "Bacterial transcript imaging by hybridization of total RNA to oligonucleotide arrays," Nature Biotechnology 16: 45-48.
Dimaria (1999) "Electron energy dependence of metal-oxide-semiconductor degradation," Applied physics letters 75(16): 2427-2428.
Fan et al. (2000) "Parallel Genotyping of Human SNPs Using Generic High-density Oligonucleotide Tag Arrays," Genome Research 10: 853-860.
Gerry et al. (1999) "Universal DNA microarray method for multiplex detection of low abundance point mutations," J. Mol. Biol. 292(2): 251-262.
Golub et al. (1999) "Molecular Classification of Cancer: Class Discovery and Class Prediction by Gene Expression Monitoring," Science 286(5439): 531-537.
Gustafsson (2000) "Surpassing the lateral resolution limit by a factor of two using structured illumination microscopy," Journal of microscopy 198(Pt 2): 82-87.
Hacia (1999) "Resequencing and mutational analysis using oligonucleotide microarrays," Nature Genetics Supplement 21: 42-47.
Hakak et al. (2001) "Genome-wide expression analysis reveals dysregulation of myelination-related genes in chronic schizophrenia," Proc. Natl. Acad. Sci. 98(8): 4746-4751.
Hell et al. (1994) "Breaking the diffraction resolution limit by stimulated emission: stimulated-emission-depletion fluorescence microscopy," Optics letters 19(11): 780-782.
Hotta et al. (2010) "Spectroscopic rationale for efficient stimulated-emission depletion microscopy fluorophores," Journal of the American Chemical Society 132: 5021-5023.
Hu et al. (1985) "Hot-electron-induced MOSFET degradation—model, monitor, and improvement," Solid-State Circuits, IEEE Journal of, SC-20(1): 295-305.

Kolmakov et al. (2010) "Red-Emitting Rhodamine Dyes for Fluorescence Microscopy and Nanoscopy," Chemistry—A European Journal 16: 158-166.
Lampe et al. (2012) "Multi-colour direct STORM with red emitting carbocyanines," Biology of the Cell 104: 229-237.
Lewis et al. (1984) "Development of a 500 Å spatial resolution light microscope: I. light is efficiently transmitted through $\lambda/16$ diameter apertures," Ultramicroscopy 13: 227-231.
Llopis et al. (1998) "Measurement of cytosolic, mitochondrial, and Golgi pH in single living cells with green fluorescent proteins," Proceedings of the National Academy of Sciences 95: 6803-6808.
Lyding et al. (1996) "Reduction of hot electron degradation in metal oxide semiconductor transistors by deuterium processing," Applied Physics Letters 68(18): 2526-2528.
Mead (1966) "Metal-semiconductor surface barriers," Solid-State Electronics 9: 1023-1033.
Meister et al. (2010) "Label-Free Imaging of Metal-Carbonyl Complexes in Live Cells by Raman Microspectroscopy," Angewandte Chemie International Edition 49: 3310-3312.
Nandakumar et al. (2009) "Vibrational imaging based on stimulated Raman scattering microscopy," New Journal of Physics 11: 033026, pp. 1-9.
Perou et al. (2000) "Molecular portraits of human breast tumours," Nature 406: 747-752.
Resch-Genger et al. (2008) "Quantum dots versus organic dyes as fluorescent labels," Nature methods 5(9): 763-775.
Rinia et al. (2008) "Quantitative label-free imaging of lipid composition and packing of individual cellular lipid droplets using multiplex CARS microscopy," Biophysical journal 95: 4908-4914.
Shoemaker et al. (1996) "Quantitative phenotypic analysis of yeast deletion mutants using a highly parallel molecular bar-coding strategy," Nature Genetics 14: 450-456.
Shipp et al. (2002) "Diffuse large B-cell lymphoma outcome prediction by gene-expression profiling and supervised machine learning," Nature Medicine 8(1): 68-74.
Shtein et al. (2002) "Effects of film morphology and gate dielectric surface preparation on the electrical characteristics of organic-vapor-phase-deposited pentacene thin-film transistors," Applied physics letters 81(2): 268-270.
Soltys et al. (1992) "Interrelationships of endoplasmic reticulum, mitochondria, intermediate filaments, and microtubules—a quadruple fluorescence labeling study," Biochemistry and Cell Biology 70: 1174-1186.
Sorokin et al. (1966) "Stimulated emission observed from an organic dye, chloro-aluminum phthalocyanine," IBM Journal of Research and Development 10(2): 162-163.
Thomas et al. (2001) "Identification of toxicologically predictive gene sets using cDNA microarrays," Mol. Pharmacol. 60(6): 1189-1194.
Underwood (2000) "Monochromators and spectrographs using varied line spacing gratings," AIP Conference Proceedings 521: 117-122.
U.S. Office Action, dated Jun. 30, 2020, corresponding to U.S. Appl. No. 15/584,018, 36 pp.
Velculescu et al. (1995) "Serial Analysis of Gene Expression," Science 270(5235): 484-487.
Vogelstein et al. (1999) "Digital PCR," Proc Natl Acad Sci USA 96(16): 9236-9241.
Wittes et al. (1999) "Searching for Evidence of Altered Gene Expression: a Comment on Statistical Analysis of Microarray Data," J. Natl. Cancer Inst. 91(5): 400-401.
Ye et al. (2001) "Fluorescent microsphere-based readout technology for multiplexed human single nucleotide polymorphism analysis and bacterial identification," Human Mutation 17(4): 305-316.
Zhang et al. (2009) "Copy Number Variation in Human Health, Disease, and Evolution," Annu. Rev. Genomics Hum. Genet. 10: 451-481.

* cited by examiner

DEVICES, METHODS, AND SYSTEMS RELATING TO SUPER RESOLUTION IMAGING

RELATED APPLICATION

This patent arises from the U.S. national stage of International Patent Application Serial No. PCT/US15/52388, having an International filing date of Sep. 25, 2015, and claims the benefit of U.S. Provisional Application Ser. No. 62/055,398, entitled "Intrinsic-Contrast Super-Resolution Optical Microscope," which was filed on Sep. 25, 2014, both of which are hereby incorporated herein by reference in their entireties.

STATEMENT REGARDING FEDERALLY SPONSORED RESEARCH OR DEVELOPMENT

This invention was made with government support under grant numbers R01EY019951, R24EY022883, and R01CA165309 awarded by the National Institutes of Health; and grant numbers DBI-1353952, CBET-1055379, CBET-1066776, EFRI-1240416, and CMMI-0955195 awarded by the National Science Foundation. The government has certain rights in the invention.

FIELD OF THE DISCLOSURE

This disclosure relates generally to characterizing biological tissue and material and, more particularly, to characterizing biological tissue and other material beyond an optical diffraction limit.

BACKGROUND

The statements in this section merely provide background information related to the disclosure and may not constitute prior art.

While electron microscopy (EM) and scanning probe microscopy (SPM) are successful and commonly adopted methods for high resolution imaging of various materials, these methods are insufficient for non-invasive imaging of internal polymer structural information and embedded materials. While both these methods can provide information on the nanoscopic scale, they often require harsh sample preparation that may either damage or destroy the imaged sample. Advantageously, optical microscopes can non-invasively discern internal features and optical signatures of materials. For example, optical microscopy can be used to monitor internal single molecule distributions and locate defects inside of crystals. However, the spatial resolution of conventional optical imaging methods is fundamentally limited by optical diffraction, far below that of EM and SPM techniques. Therefore, there is need in the art to develop super-resolution optical imaging methods.

Optically probing of diffraction limited features poses a challenge to researchers. Conventional optical imaging systems are still constrained by an optical resolution limit that is imposed by diffraction of visible light waves as they pass through a circular aperture at a rear focal plane of an objective lens. A diffraction limit of an optical device is a minimum angle between two objects that can be clearly distinguished. The diffraction limit is determined by a diameter of the optical system and a wavelength of the light being observed. For example, a diffraction limit restricts an ability of optical instruments to distinguish between two objects separated by a lateral distance less than approximately half the wavelength of light used to image the objects.

Diffraction involves spreading light waves when the light waves interact with a specimen and its structures. Due to diffraction of light, the image of a specimen does not perfectly represent all details present in the specimen because there is a lower limit below which the optical system cannot resolve structural details (referred to as the diffraction limit).

The most recent advances in super-resolution optical imaging techniques, such as stochastic optical reconstruction microscopy (STORM), photoactivated localization microscopy (PALM), stimulated emission depletion (STED), and structured illumination microscopy (SIM), may extend the ability to study sub-diffraction-limited features that were previously thought to be unresolvable and have been applied to a myriad of applications including biological imaging, medical imaging for the diagnosis of disease, optimizing lithography techniques, directly observed catalytic effects of metallic nanoparticles on a molecular scale, and tracked single polymer molecules.

These super-resolution technologies rely on extrinsic contrast agents. Extrinsic agents can have multiple weaknesses, including (1) they require additional labeling processes, (2) they modify physical properties of the target material, and (3) they introduce inaccurate spatial localization caused by the physical dimension of the tagged fluorescent and linker molecule (4), due to spectral overlap, a limited number of labels may be resolved or may confound imaging signals leading to inaccuracy. These weaknesses reduce the appeal of extrinsic fluorescent contrast agents with traditional imaging methods. There is need in the art for improved super-resolution methods that either do not require extrinsic labels, or that are able to better resolve samples with extrinsic labeling for improved imaging.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Figure 1:
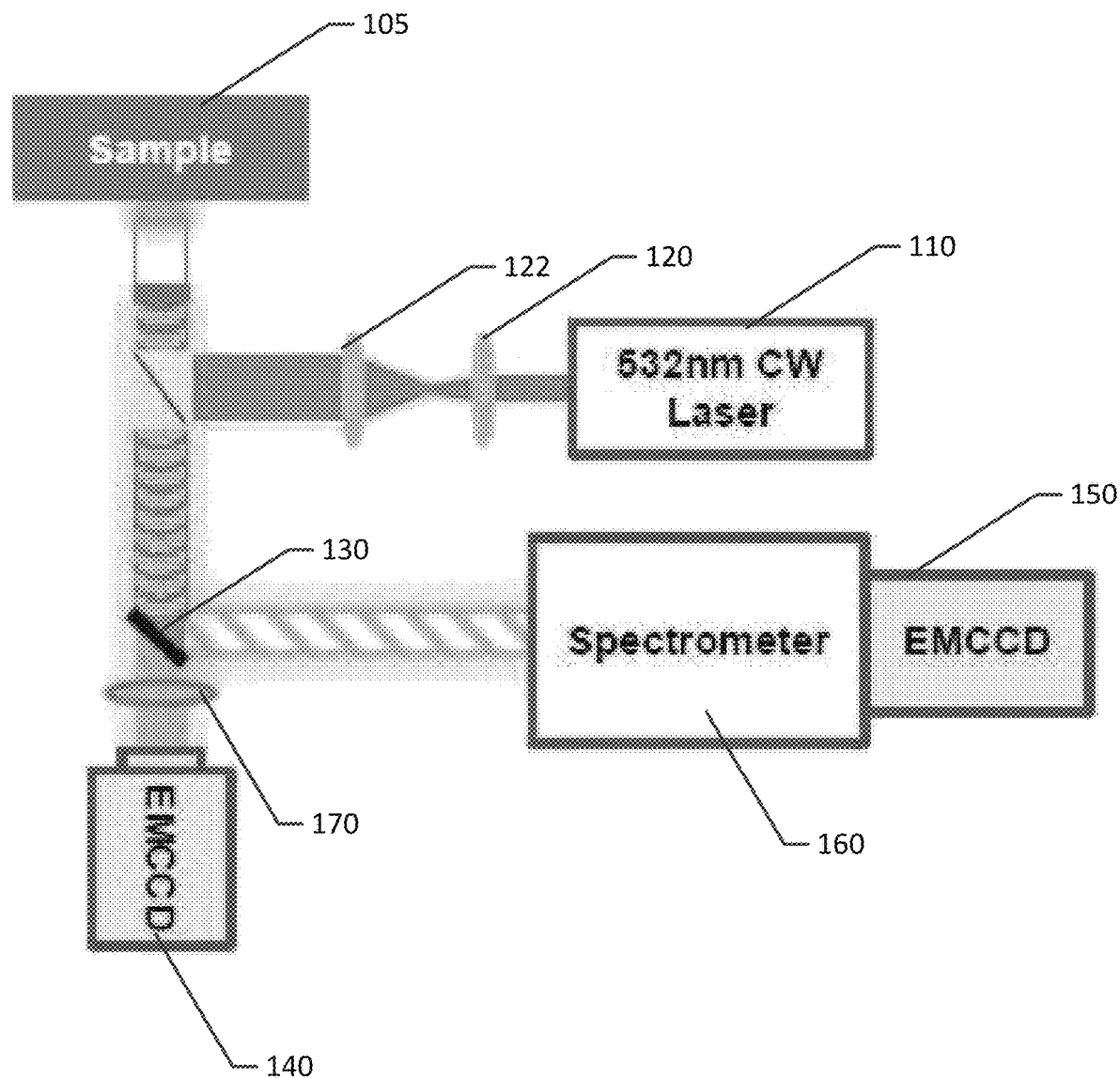
FIG. 1 illustrates an example intrinsic-contrast, super-resolution optical microscope system.

The following detailed description of certain embodiments of the present invention will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe example implementations and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Nanostructured polymers are important in both material and biological sciences. Down-scaling polymer structures to nanoscopic dimensions dramatically alters physical properties of the polymer structures and thereby alters their potential usage. Certain examples disclose new imaging methods to characterize nanoscopic polymer structures and optical properties because traditional techniques such as electron microscopy (EM) and scanning probe microscopy (SPM) have proven insufficient for non-invasive imaging of internal polymer structural information and embedded materials.

Therefore, certain examples provide super-resolution optical imaging methods using a material's intrinsic physical or chemical properties which offer unique advantages in the visualization and characterization of polymeric materials and are not restricted by spatial resolution of conventional optical imaging methods which are fundamentally limited by optical diffraction.

Certain examples provide super-resolution optical imaging methods and associated systems. For example, using a material's intrinsic physical and/or chemical properties, and/or through extrinsic labeling, unique advantages in the visualization and characterization of polymeric materials can be provided. In some examples, super resolution imaging with minimal damage or perturbation to the sample may be provided. Certain examples provide improved super-resolution methods that do not require extrinsic labels. Certain examples are able to better resolve samples with extrinsic labeling for improved imaging.

Certain examples provide systems, methods, apparatus, and the like, that combine spectroscopy with microscopy for simultaneous operation to obtain a direct image of a sample's appearance while also extracting information regarding the sample's molecules. For example, certain examples utilize a stochastic process such as spontaneous Raman scattering (e.g., intrinsic-contrast) to characterize materials and biological tissues beyond the optical diffraction limit. Certain examples provide a hybrid, Raman-STORM approach to determine sample composition and resolve features beyond the optical diffraction limit. However, other examples provide a STORM-based approach which implements a process flow to localize points of light in a sample as well as examining spectral curves associated with molecules in spectral analysis with the STORM imaging. Certain examples provide super-resolution imaging in cellular molecular imaging by eliminating a need for fluorescent staining and adding a freedom of optical molecular selectivity to obtain molecular imaging data.

In traditional STORM imaging, points of light are localized in a sample being imaged. In contrast, in certain examples disclosed herein, in addition to localizing points of light in molecules or moieties of a sample being imaged, a spectral analysis is conducted for molecules in the sample to identify and analyze spectral curves in each molecule as part of the imaging.

By simultaneously combining spectral imaging with microscopy imaging (e.g., single molecule imaging using STORM or other methodology), individual labels or spectral information for individual molecules being imaged in a sample. In contrast, traditional imaging of different spectras having different colors is limited by overlap in channels which blocks or otherwise interferes with resolution of many overlapping or adjacent channels (e.g., limited to resolving up to four colors). With the addition of the spectral information, however, a plurality of individual channels can be resolved using spectral curve information extracted from molecules/moieties.

In certain examples, individual molecule spectras are resolved using a spectral unmixing algorithm to pull apart molecule spectra and resolve each spectra individually. An additional algorithm can be applied to evaluate a linearity of the identified spectral curves. Using spectral unmixing and linearity evaluation algorithms can resolve a theoretically infinite number of spectral channels as long as the spectral channels are different enough from each other. Further, individual molecules can be resolved to associate particular spectra with particular molecules such that resolution is no longer limited by channels but rather a number of photons that can be counted given the system configuration, for example.

In certain other examples, Raman scattering is an inelastic stochastic scattering process, and multiple Raman scattering events from incident light on a molecule or crystal lattice can generate a point-spread function (PSF). The generated PSF is diffraction limited. However, using the stochastic nature of Raman scattering together with STORM reconstruction enables imaging of features beyond the diffraction limit by pin pointing a center of the spontaneous Raman PSF. Using this technique, features closer than the diffraction limited resolution can be distinguished.

In certain examples, as discussed above, a resolution limit is governed by a number of detectable photons as in STORM. As opposed to conventional fluorescence microscopy, which observes all fluorescently labeled molecules on a sample at the same time, STORM activates only a certain low percentage of molecules at any one given time. In STORM, fluorescent molecule activation is repeated to acquire multiple frames in which the molecules are localized with nanometer accuracy, and the frames are combined for a resulting final super-resolution image.

However, unlike STORM, a hybrid or modified STORM approach (e.g., Raman-STORM) relies on an intrinsic nature of materials and does not use contrast agents (e.g., fluorescents). Furthermore, by taking the Raman spectrum, a composition of the imaged material can be determined.

The point spread function (PSF) describes a response of an imaging system to a point source or point object. The PSF can also be thought of as an imaging system's impulse response, the PSF being the impulse response of a focused optical system. In certain examples, the PSF represents an unresolved object (e.g., a blob) in an image. In functional terms, the PSF is the spatial domain version of a transfer function of the imaging system. A degree of spreading (e.g., blurring) of the unresolved point object is a measure for imaging system quality.

As discussed above, stochastic optical reconstruction microscopy (STORM) relies on special photo switchable fluorescent molecules to resolve objects beyond the diffraction limit in the far-field. Raman-STORM utilizes the stochastic Raman scattering process in combination with STORM to take advantage of a low probability of fluorescent dye absorption at specific excitation wavelengths. Given that Raman scattering is an intrinsic property of each material, the material composition can be determined (e.g., its Raman spectra) and imaged beyond the diffraction limit without time constraints. In contrast, fluorescent imaging counterparts, such as STORM and PALM, suffer from time constrains and molecular attachment detection of specific molecules.

An ability to determine structural information beyond the diffraction limit has wide spread applications in material and biological studies. For example, semiconductors make possible the multi-trillion dollar electronic industry. At the heart of electronic devices are semiconductor based Metal Oxide Semiconductor (MOS) transistors. Defect-free semiconductors have better properties and longer lifetimes. Surface characteristics of semiconductors are important due to the effect they have on interfacial properties of the created MOS transistor. Rough or impure surfaces can lead to hot carrier degradation and shorter device lifetimes.

Due to the high resolution, electron microscopy is normally used in surface and interfacial studies of semiconductors. However, electron microscopy is expensive and large amounts of sample preparation are necessary using that technique. In contrast, super-resolution imaging, such as hybrid or modified STORM (e.g., Raman-STORM) allows for high-resolution optical imaging and material characterization, which is faster and less expensive than electron microscopy. Additionally, resolution of modified STORM imaging such as Raman-STORM imaging can rival the resolution of electron microscopes. Furthermore, Raman-STORM imaging can be adapted for a larger range of samples as compared to electron microscopy, for example.

Although Raman imaging provides label free imaging, it involves higher powers and longer integration times than fluorescence imaging. Lower resolution achieved through Raman imaging can be a problem when attempting to study small biological features that are beyond the resolution limit, such as mitochondria. In a small feature study, fluorescence has an advantage since molecular specific dyes can be used to target specific features, without resolving them. In fluorescence, unlike Raman scattering, even if the feature is beyond the diffraction limit, its location can at least be approximated to a relatively high accuracy. These disadvantages keep Raman microscopy from being highly employed in biological imaging.

Fluorescent dyes are normally necessary for limited optical microscopy beyond the diffraction limit. Time is highly limited in data acquisition for techniques such as STED, PALM and STORM. Furthermore, fluorescent dyes can perturb cell function with their cyto- and photo-toxicity. This perturbation can affect cell function and interaction, making conclusive studies near impossible and skewing results. Conversely, Raman-STORM and other hybrid STORM techniques offer label free molecular imaging based on detection of vibrational frequencies of molecules in living specimens. A laser can be tuned to wavelengths that have reduced or minimal cell interaction and still have sufficient intensity using a camera sensitive enough for detection. Since molecular dyes are not necessary, cyto-toxicity does not perturb the study. Use of Raman-STORM, for example, can overcome the main limitation of Raman microscopy in biology and the perturbing effect of molecular contrast agents, for example.

As disclosed and discussed further below, enhanced STORM methodologies such as Raman-STORM and other STORM-based super-resolution imaging technologies provide improved imaging resolution and accuracy. Various examples of various techniques (e.g., both Raman and non-Raman STORM-hybrids combining microscopy with spectroscopy) are described further below.

The devices, methods, and systems of the present disclosure provide for spectroscopic super-resolution microscopic imaging. In some examples, spectroscopic super-resolution microscopic imaging may be referred to as or include spectroscopic photon localization microscopy (SPLM), a method which may employ the use of extrinsic labels or tags in a target suitable for imaging. In some examples, spectroscopic super-resolution microscopic or SPLM may not employ extrinsic labels and be performed using the intrinsic contrast of the target or target material.

Generally, spectroscopic super-resolution microscopic imaging may comprise resolving one or more non-diffraction limited images of an area of a target by acquiring both localization information of a subset of molecules or moieties using microscopic methods known in the art, and simultaneously or substantially simultaneously, acquiring spectral data about the same or corresponding molecules in the subset. Together, both microscopic localization and spectral information can be used to generate one or more non-diffraction limited images. In some examples, the signal used for acquiring microscopic localization and spectral information may be derived from an extrinsic label applied to one or more molecules in the target. In some examples, the signal used for acquiring microscopic localization and spectral information may be derived from the intrinsic contrast or inherent chemical and physical properties (e.g. electronic configuration) of the target or target material.

Brief Description

Certain examples provide methods for imaging a target. An example method includes: a) activating a subset of light-emitting molecules in a wide field area of a target using an excitation light; b) capturing one or more images of the light emitted from the subset of the molecules illuminated with the excitation light; c) localizing one or more activated light emitting molecules using one or more single molecule microscopic methods to obtain localization information; d) simultaneously capturing spectral information for the same localized activated light emitting molecules using one or more spectroscopic methods; e) resolving one or more non-diffraction limited images of the area of the target using a combination of the localization and spectral information for the localized activated light emitting molecules; and f) displaying the one or more non-diffraction limited images.

Certain examples provide systems for imaging a target. An example system includes: a) one or more light sources configured to activate a subset of light-emitting molecules in a wide field area of a target; b) a microscope feature configured to capture optical images of the light-emitting molecules in an area of a target; c) a spectrometer configured to simultaneously capture spectral information for individual light-emitting molecules in an area of a target; d) a spectral filtering element; e) one or more imagers configured to capture optical images and spectral information for light-emitting molecules in an area of a target to generate one or more non-diffraction limited images of the area; and f) a display for one or more non-diffraction limited images of the area.

II. Example Methods and Systems for Spectroscopic Super-Resolution Microscopic Imaging A. Terminology In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers, elements, or steps. As used in this application, the terms "about" and "approximately" are used as equivalents. Any numerals used in this application with or without about/approximately are meant to cover any normal fluctuations appreciated by one of ordinary skill in the relevant art. In certain examples, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "spectroscopic super-resolution microscopic imaging" described herein, generally refers to any general optical imaging method that uses both microscopic single molecule localization of molecules in a target and spectroscopic information about those molecules in a target to generate one or more non-diffraction limited images. In some examples, single molecule localization of molecules and spectroscopic information is captured to resolve one or more non-diffraction limited images simultaneously.

The term "activating" refers to any change in the electronic state of a molecule. In some examples, activating may refer to excitation of the molecule to fluoresce. In some examples activating may refer to Raman scattering.

In the present disclosure, "wide-field," "wide-field area of the target," or "area," may be used interchangeably and refer generally to an area of a target where the area may be illuminated by a light source, an image of the area can be projected onto an image capture device, and the area is not confined, or masked by one or more slits or apertures. This is in contrast to conventional spectroscopic analysis as known in the art, whereby a slit, mask or aperture is used in the capturing of spectral information. In conventional spectroscopic methods as known in the art, use of slits, masks and apertures define optical resolution and throughput of a spectrometer. In the devices, methods, and systems of the disclosure, the spectra of light-emitting molecules in a wide-field area of a target illuminated by excitation light may be acquired without a slit, mask aperture, because each individual molecule emission spot may provide a sub-diffraction limited point spread function (PSF) which may already confined.

In some examples, "wide-field," "wide-field area of the target," or "area," may be used interchangeably and refer generally to an area that may be illuminated and imaged in its entirety. This is in contrast to other spectroscopic super resolution methods, whereby the area is illuminated by laser line scanning, laser spot scanning, imaging through one or more moving slits or hyperspectral imaging through the use of filters.

The term "detector" includes any detector of electromagnetic radiation including, but not limited to, a charge coupled device (CCD) camera, photomultiplier tubes, photodiodes, and avalanche photodiodes.

The term "sensor" includes any sensor of electromagnetic radiation including, but not limited to, CCD camera, photomultiplier tubes, photodiodes, and avalanche photodiodes, unless otherwise evident from the context.

The term "image", as used herein, indicates a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout). The term "image" may refer, for example, to an optical image.

The term "substantially", and grammatical equivalents, refers to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

In the present disclosure, a "target" may indicate any sample, object, or subject suitable for imaging. In some examples, a target may include but is not limited to inanimate material such as metals, alloys, polymers, and minerals as found for industrial applications for spectroscopic super-resolution microscopic imaging and as described herein. In some examples, a target may be animate material, such any suitable living material including but not limited to embryos, seeds, one or more cells, tissues, grafts, blood vessels, organs, or organisms as would be suitable for medical and agricultural applications for spectroscopic super-resolution microscopic imaging as described herein. In some examples, a target may be a moiety that one wishes to observe or quantitate. A target, in some examples, may be non-naturally occurring. The target, in some examples, may be a biomolecule. As used herein, a "biomolecule" is any molecule that is produced by a living organism, including large macromolecules such as proteins, polysaccharides, lipids and nucleic acids (e.g., DNA and RNA such as mRNA), as well as small molecules such as primary metabolites, secondary metabolites, and natural products. Examples of biomolecules include, without limitation, DNA, RNA, cDNA, or the DNA product of RNA subjected to reverse transcription, protein, lipid, fats, small molecules, and carbohydrates.

In the present disclosure, "light emitting molecules" may indicate any molecule that can emit a photon at any wavelength. In some examples, a light-emitting molecule may be a fluorophore. In some cases, a light-emitting molecule emits a photon after illumination and excitation with one or more wavelengths of light.

In the present disclosure, "extrinsic labels" may be molecules or specific probes that emit signals detected during spectroscopic super-resolution microscopic. In some examples, an extrinsic label may be covalently bound to a molecule, thus making the entire molecular entity a light-emitting molecule. In some examples, an extrinsic label may be one or more non-covalently bound to a molecule, also making the entire molecular entity a light-emitting molecule. Any labels suitable for generating such signals can be used in the present disclosure. In some examples, the signals are generated by fluorophores.

Fluorescent labeling, e.g., the process of covalently attaching a fluorophore to a probe that binds to another molecule or cellular constituent (such as a protein or nucleic acid) is generally accomplished using a reactive derivative of the fluorophore that selectively binds to a functional group contained in the target molecule. The molecule may also be bound non-covalently though the use of antibodies. In some example, the fluorophore is a quantum dot. In some examples, probes to which the labels are attached include but are not limited to antibodies, proteins, amino acids and peptides. Common reactive groups include amine reactive isothiocyanate derivatives such as FITC and TRITC (derivatives of fluorescein and rhodamine), amine reactive succinimidyl esters such as NHS-fluorescein, and sulfhydryl reactive maleimide activated fluors such as fluorescein-5-maleimide.

Following a fluorescent labeling reaction, it is often necessary to remove any non-reacted fluorophore from the labeled target molecule. This can be accomplished by size exclusion chromatography, taking advantage of the size difference between fluorophore and labeled protein, nucleic acid, etc. Fluorophores may interact with a separation matrix and reduce the efficiency of separation. For this reason, specialized dye removal columns that account for the hydrophobic properties of fluorescent dyes can be used. Reactive fluorescent dyes are available from many sources. The dyes can be obtained with different reactive groups for attachment to various functional groups within the target molecule. Dyes are also available in labeling kits that contain all the components to carry out a labeling reaction.

In some examples, labels include one or more fluorescent dyes, including but not limited to fluorescein, rhodamine, Alexa Fluors, DyLight fluors, ATTO Dyes (or any analogs or derivatives thereof), fluorescent tag, fluorescent protein, fluorophore, fluorescent probe, quantum dot, fluorescence resonance energy transfer probe, and diode laser excitable probe used with any dyes or other labels as described herein.

In some examples, labels include but are not limited to fluorescein and chemical derivatives of fluorescein; Eosin; Carboxyfluorescein; Fluorescein isothiocyanate (FITC); Fluorescein amidite (FAM); Erythrosine; Rose Bengal; fluorescein secreted from the bacterium Pseudomonas aeruginosa; Methylene blue; Laser dyes; Rhodamine dyes (e.g., Rhodamine, Rhodamine 6G, Rhodamine B, Rhodamine 123, Auramine O, Sulforhodamine 101, Sulforhodamine B, and Texas Red).

In some examples, labels include but are not limited to ATTO dyes; Acridine dyes (e.g., Acridine orange, Acridine yellow); Alexa Fluor; 7-Amino actinomycin D; 8-Anilinonaphthalene-1-sulfonate; Auramine-rhodamine stain; Benzanthrone; 5,12-Bis(phenylethynyl)naphthacene; 9,10-Bis(phenylethynyl)anthracene; Blacklight paint; Brainbow; Calcein; Carboxyfluorescein; Carboxyfluorescein diacetate succinimidyl ester; Carboxyfluorescein succinimidyl ester; 1-Chloro-9,10-bis(phenylethynyl)anthracene; 2-Chloro-9,10-bis(phenylethynyl)anthracene; 2-Chloro-9,10-diphenylanthracene; Coumarin; Cyanine dyes (e.g., Cyanine such as Cy3 and Cy5, DiOC6, SYBR Green I); DAPI, Dark quencher, DyLight Fluor, Fluo-4, FluoProbes; Fluorone dyes (e.g., Calcein, Carboxyfluorescein, Carboxyfluorescein diacetate succinimidyl ester, Carboxyfluorescein succinimidyl ester, Eosin, Eosin B, Eosin Y, Erythrosine, Fluorescein, Fluorescein isothiocyanate, Fluorescein amidite, Indian yellow, Merbromin); Fluoro-Jade stain; Fura-2; Fura-2-acetoxymethyl ester; Green fluorescent protein, Hoechst stain, Indian yellow, Indo-1, Lucifer yellow, Luciferin, Merocyanine, Optical brightener, Oxazin dyes (e.g., Cresyl violet, Nile blue, Nile red); Perylene; Phenanthridine dyes (Ethidium bromide and Propidium iodide); Phloxine, Phycobilin, Phycoerythrin, Phycoerythrobilin, Pyranine, Rhodamine, Rhodamine 123, Rhodamine 6G, RiboGreen, RoGFP, Rubrene, SYBR Green I, (E)-Stilbene, (Z)-Stilbene, Sulforhodamine 101, Sulforhodamine B, Synapto-pHluorin, Tetraphenyl butadiene, Tetrasodium tris(bathophenanthroline disulfonate)ruthenium(II), Texas Red, TSQ, Umbelliferone, or Yellow fluorescent protein.

In some examples, labels include but are not limited to the Alexa Fluor family of fluorescent dyes (Molecular Probes, Oregon). Alexa Fluor dyes are typically used as cell and tissue labels in fluorescence microscopy and cell biology.

The excitation and emission spectra of the Alexa Fluor series cover the visible spectrum and extends into the infrared. The individual members of the family are numbered according roughly to their excitation maxima (in nm). Alexa Fluor dyes are synthesized through sulfonation of coumarin, rhodamine, xanthene (such as fluorescein), and cyanine dyes. Sulfonation makes Alexa Fluor dyes negatively charged and hydrophilic. Alexa Fluor dyes are generally more stable, brighter, and less pH-sensitive than common dyes (e.g. fluorescein, rhodamine) of comparable excitation and emission, and to some extent the newer cyanine series. Example Alexa Fluor dyes include but are not limited to Alexa-350, Alexa-405, Alexa-430, Alexa-488, Alexa-500, Alexa-514, Alexa-532, Alexa-546, Alexa-555, Alexa-568, Alexa-594, Alexa-610, Alexa-633, Alexa-647, Alexa-660, Alexa-680, Alexa-700, or Alexa-750.

In some examples, labels include one or more members of the DyLight Fluor family of fluorescent dyes (Dyomics and Thermo Fisher Scientific). Example DyLight Fluor family dyes include but are not limited to DyLight-350, DyLight-405, DyLight-488, DyLight-549, DyLight-594, DyLight-633, DyLight-649, DyLight-680, DyLight-750, or DyLight-800.

In some examples, when pairs of dyes are used, the activator choices include Alexa405, 488, 532 and 568, and the emitter choices include Cy5, Cy5.5, Cy7, and 7.5. Using these particular choices, because they can be mixed and matched to give functional dye pairs, there are 16 possible pairs (4×4) in all.

In some examples, a light-emitting molecule may be stochastically activated. In some examples, stochastically activated may comprise photoswitching, or stochastic emission of light ("blinking"). In some examples, a switchable entity may be used. Non-limiting examples of switchable entities are discussed in International Patent Application No. PCT/US2007/017618, filed Aug. 7, 2007, entitled "Sub-Diffraction Limit Image Resolution and Other Imaging Techniques," published as International Patent Application Publication No. WO 2008/091296 on Jul. 31, 2008, which is incorporated herein by reference. As a non-limiting example of a switchable entity, Cy5 can be switched between a fluorescent and a dark state in a controlled and reversible manner by light of different wavelengths, e.g., 633 nm or 657 nm red light can switch or deactivate Cy5 to a stable dark state, while 532 nm green light can switch or activate the Cy5 back to the fluorescent state. Other non-limiting examples of a switchable entity including photoactivatable or photoswitchable fluorescent proteins, or photoactivatable or photoswitchable inorganic particles, e.g., as discussed herein. In some examples, the entity can be reversibly switched between the two or more states (e.g., upon exposure to the proper stimuli). For example, a first stimuli (e.g., a first wavelength of light) may be used to activate the switchable entity, while a second stimuli (e.g., a second wavelength of light) may be used to deactivate the switchable entity, for instance, to a non-emitting state. Any suitable method may be used to activate the entity. For example, in one example, incident light of a suitable wavelength may be used to activate the entity to emit light (that is, the entity is photoswitchable). Thus, the photoswitchable entity can be switched between different light-emitting or non-emitting states by incident light (e.g., of different wavelengths). The light may be monochromatic (e.g., produced using a laser) or polychromatic. In another example, the entity may be activated upon stimulation by electric field and/or magnetic field. In other examples, the entity may be activated upon exposure to a suitable chemical environment (e.g., by adjusting the pH, or inducing a reversible chemical reaction involving the entity, etc.). Similarly, any suitable method may be used to deactivate the entity, and the methods of activating and deactivating the entity need not be the same. For instance, the entity may be deactivated upon exposure to incident light of a suitable wavelength, or the entity may be deactivated by waiting a sufficient time.

In some examples, the switchable entity may include a first, light-emitting portion and a second, activation portion, as discussed herein. In one set of examples, the switchable entity can be immobilized (e.g., covalently, with respect to a binding partner such as a molecule that can undergo binding with a particular analyte). Binding partners include specific, semi-specific, and nonspecific binding partners as known to those of ordinary skill in the art. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologies). Thus, for example, in the case of a receptor/ligand binding pair, the ligand would specifically and/or preferentially select its receptor from a complex mixture of molecules, or vice versa. Other examples include, but are not limited to, an enzyme would specifically bind to its substrate, a nucleic acid would specifically bind to its complement, and an antibody would specifically bind to its antigen. The binding may be by one or more of a variety of mechanisms including, but not limited to ionic interactions, and/or covalent interactions, and/or hydrophobic interactions, and/or van der Waals interactions, etc. By immobilizing a switchable entity with respect to the binding partner of a target molecule or structure (e.g., DNA or a protein within a cell), the switchable entity can be used for various determination or imaging purposes. For example, a switchable entity having an amine-reactive group may be reacted with a binding partner comprising amines, for example, antibodies, proteins or enzymes.

In some examples, more than one switchable entity may be used, and the entities may be the same or different. In some examples, the light emitted by a first entity and the light emitted by a second entity have the same wavelength. The entities may be activated at different times, and the light from each entity may be determined separately. This allows the location of the two entities to be determined separately, and, in some examples, the two entities may be spatially resolved, as described herein, even at distances of separation that are less than the light emitted by the entities or below the diffraction limit of the emitted light (e.g., resolving "non-diffraction limited" images). In certain instances, the light emitted by a first entity and the light emitted by a second entity have different wavelengths (for example, if the first entity and the second entity are chemically different, and/or are located in different environments). The entities may be spatially resolved even at distances of separation that are less than the light emitted by the entities or below the diffraction limit of the emitted light. In certain instances, the light emitted by a first entity and the light emitted by a second entity have substantially the same wavelengths, but the two entities may be activated by light of different wavelengths and the light from each entity may be determined separately. The entities may be spatially resolved even at distances of separation that are less than the light emitted by the entities, or below the diffraction limit of the emitted light.

In some examples, the first, light-emitting portion and the second, activation portion as described above may not be directly covalently bonded or linked via a linker, but are each immobilized relative to a common entity. In other examples, two or more of the switchable entities (some of which can include, in certain cases, a first, light-emitting portion and a second, activation portion linked together directly or through a linker) may be immobilized relative to a common entity in some aspects of the present disclosure. The common entity in any of these examples may be any nonbiological entity or biological entity, for example, a cell, a tissue, a substrate, a surface, a polymer, a biological molecule such as a nucleic acid (DNA, RNA, PNA, LNA, or the like), a lipid molecule, a protein or a polypeptide, or the like, a biomolecular complex, or a biological structure, for example, an organelle, a microtubule, a clathrin-coated pit, etc. The common entity may accordingly be determined in some fashion, e.g., imaged. As another example, two or more entities may be immobilized relative to a DNA strand or other nucleic acid strand (e.g., using antibodies, substantially complementary oligonucleotides labeled with one or more entities, chemical reactions or other techniques known to those of ordinary skill in the art), and their locations along the strand detected. In some cases, the number of base pairs (bp) separating the entities along the nucleic acid strand may be determined.

In some cases, the entities may be independently switchable (e.g., the first entity may be activated to emit light without activating a second entity). For example, if the entities are different, the methods of activating each of the first and second entities may be different (e.g., the entities may each be activated using incident light of different wavelengths). As another non-limiting example, incident light having a sufficiently weak intensity may be applied to the first and second entities such that only a subset or fraction of the entities within the incident light are activated (e.g., on a stochastic or random basis). Specific intensities for activation can be determined by those of ordinary skill in the art using no more than routine skill. By appropriately choosing the intensity of the incident light, the first entity may be activated without activating the second entity.

The second entity may be activated to emit light, and optionally, the first entity may be deactivated prior to activating the second entity. The second entity may be activated by any suitable technique, as described herein, for instance, by application of suitable incident light.

In some cases, incident light having a sufficiently weak intensity may be applied to a plurality of entities such that only a subset or fraction of the entities within the incident light are activated (e.g., on a stochastic or random basis). The amount of activation may be any suitable fraction or subset of entities (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the entities may be activated), depending on the application. For example, by appropriately choosing the intensity of the incident light, a sparse subset of the entities may be activated such that at least some of them are optically resolvable from each other and their positions can be determined. Iterative activation cycles may allow the positions of all of the entities, or a substantial fraction of the entities, to be determined. In some examples, an image with non-diffraction limit resolution can be constructed using this information.

In the present disclosure, "intrinsic contrast" refers to detection of light emission without the use of an extrinsic label. In some examples, an extrinsic label may not be applied to target. In some examples, light-emitting molecules in an area of a target are not subject to an extrinsic label. In some examples, molecules within the target my emit photons, or fluoresce without the need of an extrinsic label. For example, certain polymers may have suitable absorption-emission bands such that individual molecules, or subunits within the polymer emit light when excited by a suitable wavelength of light. Generally, detection of light emission without the use of extrinsic labels may be referred to as intrinsic contrast.

Any light-emitting target may be suitable for spectroscopic super-resolution microscopic imaging using intrinsic contrast. Examples of light emitting polymers may be imaged using spectroscopic super-resolution microscopic imaging include but are not limited to: ITO, MEH-PPV, PEDOT:PSS, PVDF, PPY, SU8, PMMA and PS. Other examples of biological light-emitting polymers that may be imaged as a suitable target using spectroscopic super-resolution microscopic imaging include but are not limited to: protein, lipids, nucleic acids, DNA, RNA, carbohydrates, or fats.

In some examples, light emitting may be the result of any perturbation or change in the electronic state of the target. In some examples, and as described herein, a perturbation or change in the electronic state of target might result in fluorescence. In some examples, any perturbation or change in the electronic state of the target may result in Raman scattering. Generally, the devices, methods, and systems of the disclosure provide for use of signals from any light-emitting molecules, including but not limited to Raman spectroscopy, optical fluorescence microscopy, infrared spectroscopy, ultraviolet spectroscopy, laser microscopy and confocal microscopy.

B. Example Raman-STORM Methods

Certain examples provide methods for image reconstruction beyond the diffraction limit based on hybrid Raman-STORM methodologies. For example, a maximum resolvable distance, $\Delta x$, is a closest distance at which two features can be and still be distinguished from each other. The maximum resolvable distance is directly related to an incident wavelength, $\lambda_o$, and inversely related to the numerical aperture (N.A.) of the objective. According to Rayleigh criterion:

$$\Delta x = 0.61 \frac{\lambda_O}{N.A.}. \qquad \text{(Eq. 1)}$$

Since visible light is in the range of 400-700 nm and an approximate value of the highest N.A. objectives is 1.5, a highest theoretical resolution in a visible region is around 160 nm. In certain examples, this poses a problem for imaging fine features of materials.

In fluorescence imaging, when molecules emit radiation simultaneously, a distance between individual molecules cannot be determined due to overlapping PSF. In normal circumstances, a density of molecules is very high, making it impossible to distinguish a location of individual fluorescing molecules among other nearby fluorescing molecules. When molecules have a low absorption cross-section from incident light, a probability of emission decreases greatly. However, with large amounts of time, the molecules will eventually fluoresce, leading to a "blinking" type of process.

STORM uses immunolabeling of the sample with antibodies tagged with organic fluorophores. The fluorophores are driven by light between an active-on state and an inactive-off state. In STORM, stochastic photoblinking of the organic fluorophores (typically brighter than fluorescent proteins) can be exploited to separate neighboring dyes.

Since a likelihood of two fluorescing events taking place in a same localized region is small, a detected fluorescence PSF can be assumed to occur from a single molecule. Depending on a number of detected photons (N), a standard deviation of the point-spread function ($s_i^2$), an average background signal of the detector ($b^2$), and a pixel size of an imaging detector (a), a local precision of the PSF ($\sigma$) can be determined by:

$$\sigma = \sqrt{\left(\frac{s_i^2 + \frac{a^2}{12}}{N}\right) * \left(\frac{16}{9} + \frac{8\pi s_i^2 b^2}{a^2 N}\right)}. \qquad (Eq.\ 2)$$

Using Equation 2, the higher the precision of the PSF, the higher the resolution of the imaged object and features in close proximity can be determined.

In certain examples, a STORM microscopy algorithm (e.g., an algorithm fitting Gaussian kernels, etc.) compares each acquired image with a previous image including a comparison of intensity differences between the images. By comparing images, pixels that significantly differ (e.g., differ by more than a certain threshold) between the current image and the previous image are identified and matched against an average background intensity. Intensity data for pixels that differ above the threshold and are higher than the average background intensity are fitted with a Gaussian PSF. Localized precision is used to determine a specific point at which the radiation originated. By repeating the process over a large number of frames, an image that is beyond the diffraction limit can be reconstructed.

Similar to the stochastic fluorescence process of specific molecular dyes used in STORM and PALM, Raman scattering is also a stochastic process. An intensity of Raman scattering is determined by the Raman cross-section ($\sigma_{Raman}$), which is directly related to a polarizability of the material and related to an incident wavelength ($\lambda_o$) by an inverse fourth power. A relationship of the Raman cross-section to polarizability and incident wavelength can be represented as:

$$\sigma_{Raman} \propto (v_o \pm v_j)^4, \qquad (Eq.\ 3)$$

$$I_R = \mu(v_o \pm v_j)^4 \alpha_j^2 Q_j^2 \Rightarrow I_R \propto \frac{1}{\lambda_o^4}, \qquad (Eq.\ 4)$$

where $v_o$ is an incident frequency of the light, $v_j$ is a frequency of a $j^{th}$ mode of the material, $I_R$ is a Raman intensity, $\mu$ is a reduced mass, $\alpha$ is a polarizability, and Q is a displacement.

Raman scattering is a nonlinear effect of materials and is therefore generally small compared to linear radiation processes. In certain examples, a cross-section is small and a probability of radiation from individual nearby molecules is unlikely. Raman scattering events also generate PSFs similar to fluorescence. By localizing a center of the Raman generated PSF with the STORM algorithm (e.g., using Raman cross-section and Raman intensity), images can be reconstructed beyond the diffraction limit.

FIG. 1 illustrates an example intrinsic-contrast, super-resolution optical microscope system 100. The example micro-Raman system 100 includes a sample 105 imaged using a light source 110 (e.g., a continuous wave laser) generating light (e.g., 532 nm wavelength laser) which is passed through a power objective pair of lenses 120, 122 (e.g., numerical aperture or N.A.=1.5). A flip mirror 130 switches between Raman imaging using a camera 140, such as a charge coupled device (CCD) (e.g., an electron multiplying CCD (EMCCD), etc.) and Raman spectra acquisition using a camera 150 (e.g., an EMCCD or other imaging CCD, etc.) and spectrometer 160.

A long pass filter 170 (e.g., a 550 nm long pass filter) can be positioned in front of the imaging CCD 140 to filter the incident beam and collect only Raman signal, for example. The spectrometer 160 detects Raman spectrum from the sample 105. Single walled carbon nanotubes (CNTs) deposited on glass can be used for calibration and validation, for example. CNTs are used due to their large Raman cross-section, allowing for reduced or minimal acquisition times, for example. A calculated PSF changes in consecutive frames to show the stochastic blinking process of Raman scattering.

Using the system 100, a CNT spectrum can be collected from the sample 105 and compared to historical data. Confirmation of the stochastic Raman scattering process can be facilitated by comparing the PSF of consecutive images across a specific pixel array of the imaging CCD detector 140. It can be seen that the PSF changes from frame to frame, demonstrating the stochastic Raman scattering from the CNTs. If the processes are not stochastic, the PSF is present and similar in all frames.

The Raman cross-section of most materials is relatively low as compared to CNTs. In order to perform STORM on such materials it may be necessary to use fewer frames per second or take a larger number of exposures, for example.

The Raman microscopy and spectroscopy system 100 can be used to show the stochastic process of Raman scattering, and can be used to improve or optimize STORM algorithm parameters. Using the example system 100, Raman-STORM can be applied to a sample 105 of carbon nanotubes deposited on a glass substrate, for example. In an example, single walled CNTs of approximately 1.9 nm diameter are deposited on a glass slide. Brightfield and basic Raman microscopy are performed to obtain diffraction limited images. Optical scattering can be seen from the brightfield image, although feature details are not possible. Due to the small size, CNTs are difficult to image in brightfield. Raman microscopy shows CNT features clearer than brightfield images, but the diffraction limit is still present. The STORM algorithm can be used to reconstruct the image frames. A pseudo-color image can be used in the reconstructed CNT Raman-STORM image, for example. Using Raman-STORM, fine features (e.g., at a dimensional resolution of ≤40 nm) can be resolved in the image reconstruction, achieving beyond diffraction limit imaging from stochastic spontaneous Raman applied to STORM reconstruction.

Figure 2:
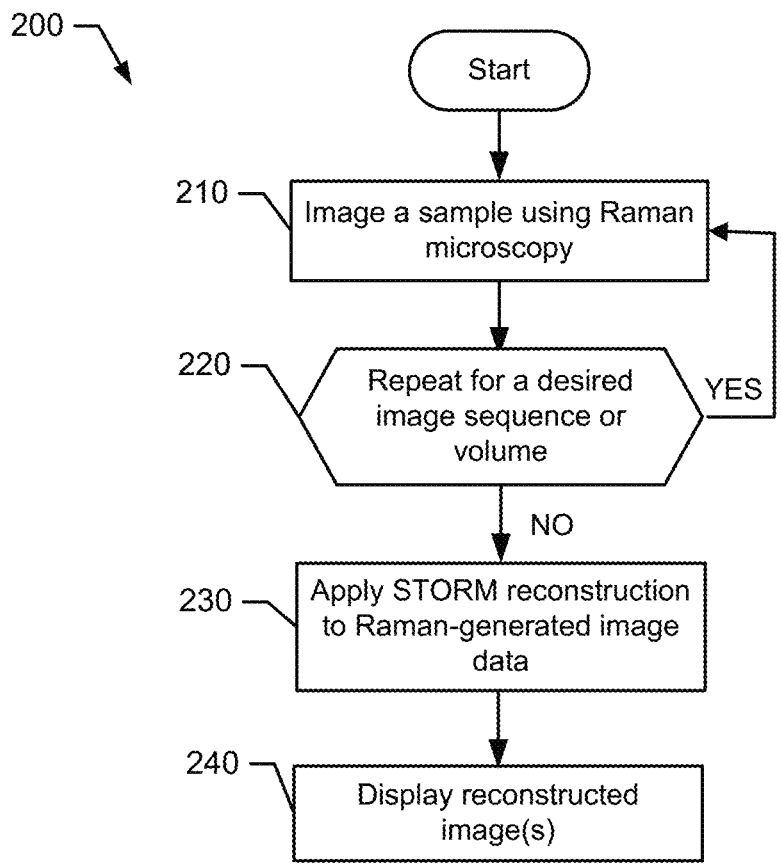
FIG. 2 illustrates a flow diagram of an example method to perform Raman-STORM imaging of a sample.

FIG. 2 illustrates a flow diagram of an example method 200 to perform Raman-STORM imaging of a sample. At block 210, a sample positioned with respect to a detector (e.g., a CCD) is imaged using Raman microscopy to obtain a diffraction limited image.

Raman scattering, an inelastic process that reveals molecular vibrational signatures, is well suited for molecular imaging. Without the presently described technology, using Raman scattering to measure molecular signatures beyond the optical diffraction limit was challenging. Most efforts have focused on enhancing a weak Raman signal using stimulated processes or near-field optical effects. However, by utilizing a "blinking" generated by Raman scattering from organic molecules localization-based super-resolution imaging can be achieved. Using weak Raman scattering provides intrinsic contrast between molecules and also directly satisfies the stochastic requirement for STORM, eliminating the need for attaching (and modifying) target molecules with fluorescent molecules. In contrast to many technology-driven projects, where new technologies seek applications, R-STORM can be used to sense cancer remotely.

For example, a diffraction limited image based on Raman scattering can be generated by comparing pixel values and intensities to generate a PSF using a Raman cross-section and Raman intensity of the sample (e.g., Equations 3 and 4). At block 220, Raman microscopy can be repeated as in block 210 for one or more additional frames for a desired image sequence or volume.

At block 230, STORM reconstruction is applied to the set of one or more diffraction limited images. Using a STORM algorithm (e.g., provided via an application such as Quick-PALM ImageJ plugin, etc.,), a Raman-generated PSF resulting from the Raman microscopy obtained at block 210 is localized to reconstruct image(s) beyond the diffraction limit. At block 240, the reconstructed image(s) are displayed.

Thus, certain examples disclosed and described herein provide systems and methods of molecular super-resolution imaging to enable nanoscopic pre-disease investigation. Certain examples provide molecule-specific super-resolution optical imaging in whole cells. Certain examples facilitate imaging without fluorescence staining, which perturbs target molecules and risks inaccurate results. Using Raman-STORM or R-STORM hybrid imaging, super-resolution technology leverages chemically-specific Raman detection, bypassing a need for fluorescent staining. The hybrid R-STORM tool combines stochastic optical reconstruction microscopy (STORM) with band-selected Raman detection in an imaging entity. R-STORM provides tunable molecular selectivity, particularly to analyze early intracellular changes involved in disease. In an example, R-STORM can help uncover "field carcinogenesis" observed in several cancers, when histologically-normal cells located far from tumors signal disease through intracellular nanoscopic alterations.

Existing super-resolution relies on photo-switchable fluorescent staining, which not only modifies the target biomolecule and perturbs its microenvironment, but also introduces inaccurate spatial localization due to the sizes of both the fluorescent and linker proteins. In contrast, analyzing intrinsic spontaneous Raman scattering from target biomolecules using R-STORM avoids the detriments of fluorescent labeling while maintaining molecular selectivity. Using weak, spontaneous Raman scattering without local enhancement provides randomness in photon localization super-resolution imaging. Using Raman scattering with STORM analysis in a hybrid R-STORM configuration can help achieve staining-free molecular imaging beyond optical diffraction. Using R-STORM can help uncover intracellular nanoscopic alterations prior to disease onset, driving a paradigm shift in understanding and early diagnosis of several significant diseases, including field carcinogenesis in early cancers. For example, R-STORM can be used to investigate chromatin structure alterations in Pap-smear samples and to correlate detected nanoscopic alterations with ovarian cancer staging.

Certain examples provide an inverted imaging system based on a total internal reflection fluorescence (TIRF) platform. Using the TIRF platform eliminates a need for spatial discrimination along a depth direction so that the focus can be on the molecular selectivity aspect of R-STORM. By comparing tissue samples with nanofabricated samples, target molecule concentration can be identified as much lower in the tissue samples and often having overlapping dominating Raman peaks. Parameters can be modified or otherwise optimized in optical illumination, emission spectrum selecting, and detection to achieve improved or maxim sensitivity for a plurality of selected biomolecules.

C. Example Super-Resolution Imaging Methods and Systems

In other examples, rather than relying on Raman scattering, nanoscopic optical imaging can be used to image buried polymer nanostructures without the need for extrinsic staining. In certain examples, spatial-temporal spectral analysis is performed to understand an origin of discovered intrinsic stochastic fluorescence emission from unstained polymers. By applying photon localization super-resolution imaging principles, half-pitch resolutions beyond an optical diffraction limit (e.g., half-pitch resolutions beyond 100 nm, which corresponds to a six-fold increase over the corresponding optical diffraction limit, etc.) are achieved. Using such imaging, static heterogeneities of intrinsic polymer molecular-specific properties can be analyzed at sub-diffraction resolutions.

Figure 3:
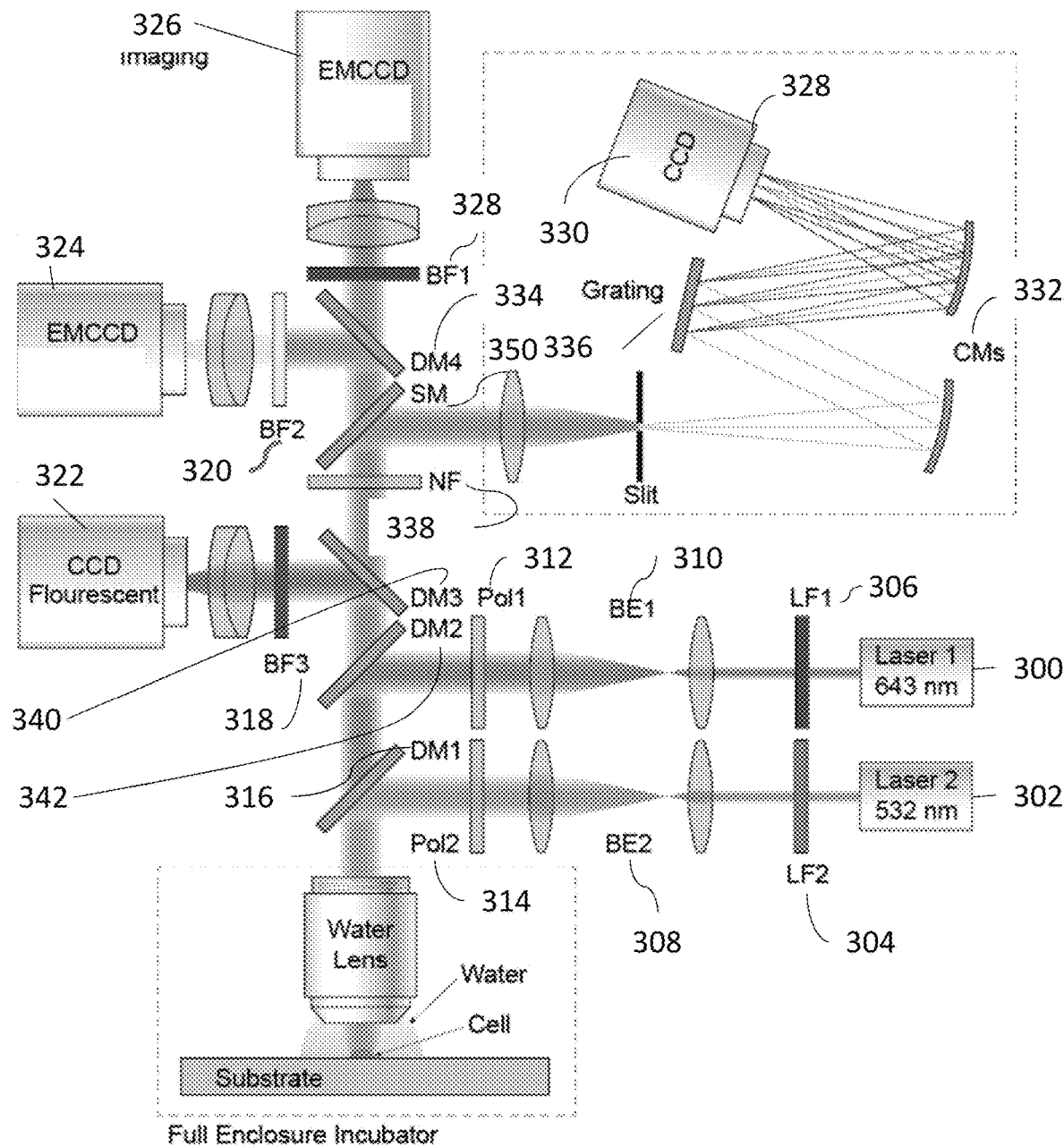
FIG. 3 shows a schematic of an example dual laser system suitable for spectroscopic super-resolution microscopic imaging.

A spectroscopic super-resolution microscopic system for data collection may be configured in a variety of ways, generally incorporating optical components capable of simultaneously performing single molecule microscopic localization and spectroscopy on a target. FIG. 3 illustrates an example system configured with multiple light sources. Light sources 300, 302 (e.g., lasers, etc.) emit light with an excitation frequency that converts molecules in a target sample, or subset of molecules in the sample, into an active state. In some example, the excitation frequency causes those molecules to fluoresce. In the example system configuration of FIG. 3, light is passed through multiple elements including but not limited to: laser line filters (LF) 306, 304; beam expanders (BE) 310, 308; polarizer (Pol) 312, 314. Light passes through these element onto a sample (e.g., a cell in water, etc.) through dichroic mirrors (DM) 340, 342, 316, 334); a notch filter (NF) 338; switchable mirror (SM) 350; a band pass filter (BF) 328, 320, 318; through a spectral filtering element (e.g., a grating, etc.); and onto a concave mirror (CM) 332. Spectroscopic and microscopic information may be collected using any suitable camera or imaging device, including but not limited to a charge coupled device (CCD) 328, 322 or electron multiplying charge coupled device (EMCCD) 324, 326, for example.

Figure 4:
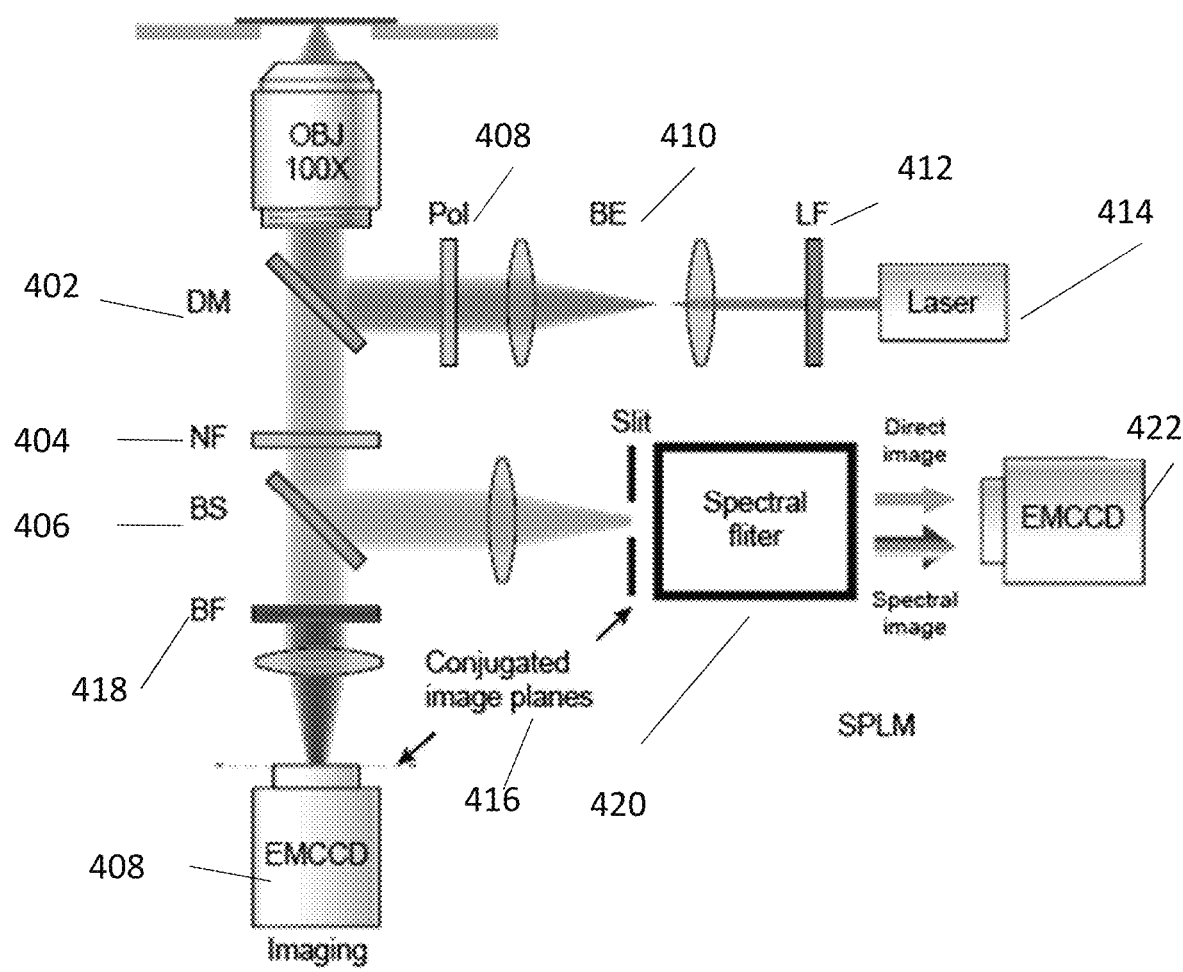
FIG. 4 shows a schematic of an example single laser system suitable for spectroscopic super-resolution microscopic imaging.

FIG. 4 illustrates another example system configured with a single light source. The light source 414 (e.g., a laser, etc.) emits light with an excitation frequency that converts molecules in the sample, or subset of molecules in the sample, into an active state. In some examples, the excitation frequency causes those molecules to fluoresce. In the example system configuration of FIG. 4, light is passed through multiple elements including but not limited to: a laser line filter 412, beam splitter 406; beam expanders (BE) 410; polarizer (Pol) 408; dichroic mirrors, (DM) 402; a notch filter (NF) 404; a band pass filter (BF) 418; and a spectral filtering element 420. Spectroscopic and microscopic information may be collected using any suitable camera or imaging device, including but not limited to an electron multiplying charged coupled device 422, 424. In some examples, light is passed through a slit that is configured with one or more imagers, such as an EMCCD 424, to produce conjugated image planes 416.

Figure 5:
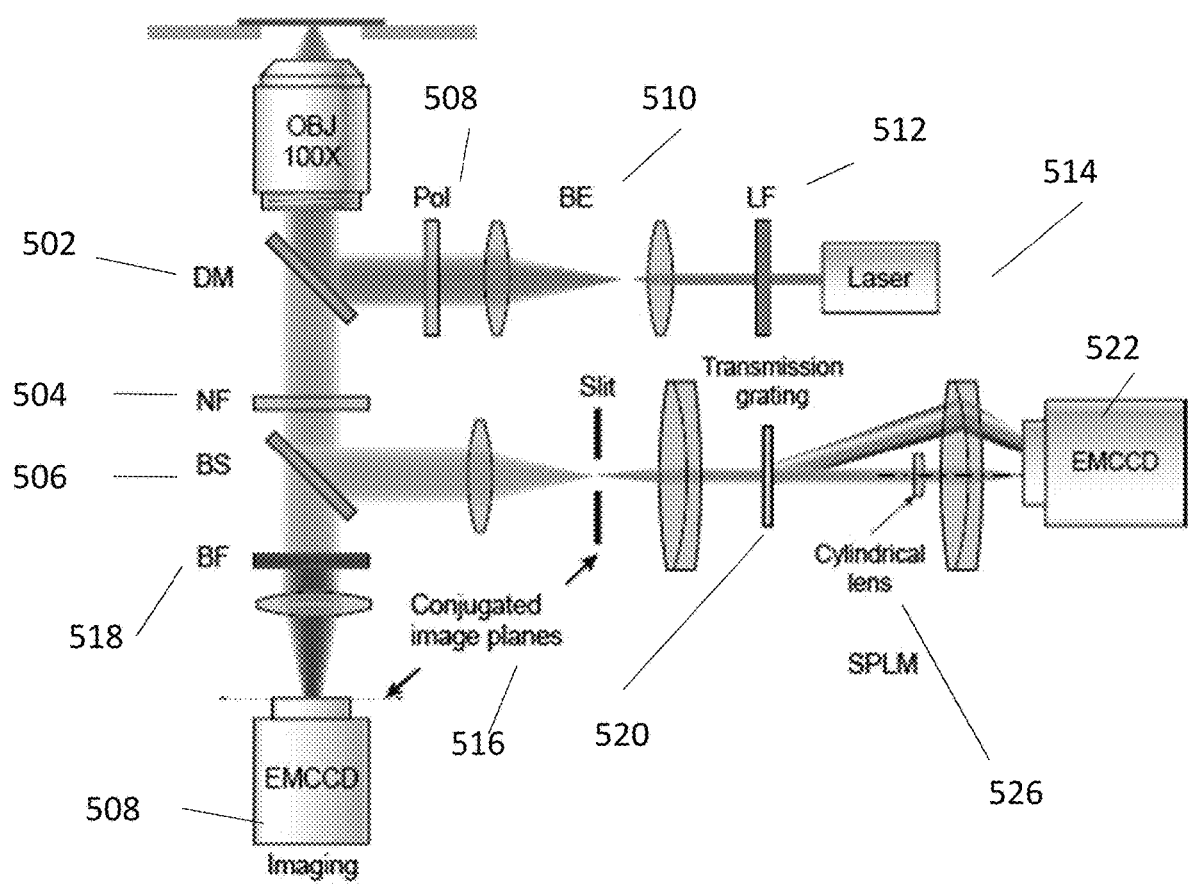
FIG. 5 shows a schematic of an example spectroscopic super-resolution microscopic imaging system configured with a cylindrical lens.

FIG. 5 illustrates another example system configured with a single light source and configured for three dimensional (3D) spectroscopic super-resolution microscopic imaging. The light source 514 (e.g., a laser, etc.) emits light with an excitation frequency that converts molecules in the sample, or subset of molecules in the sample, into an active state. In some examples, the excitation frequency causes those molecules to fluoresce. In the example system configuration of FIG. 5, light is passed through multiple elements including but not limited to: a laser line filter 512; beam splitter 506; beam expanders (BE) 510; polarizer (Pol) 508; dichroic mirrors (DM) 502; a notch filter (NF) 504; a band pass filter (BF) 518; and a spectral filtering element (e.g. a transmission grating) 520. Spectroscopic and microscopic information may be collected using any suitable camera or imaging device, including but not limited to an electron multiplying charge coupled device 522, 524. In some examples, light is passed through a slit that is configured with one or more imagers, such as the EMCCD 424, to produce conjugated image planes 516. A cylindrical lens 526 may also be used to allow for 3D spectroscopic super-resolution microscopic imaging of a target.

Figure 6:
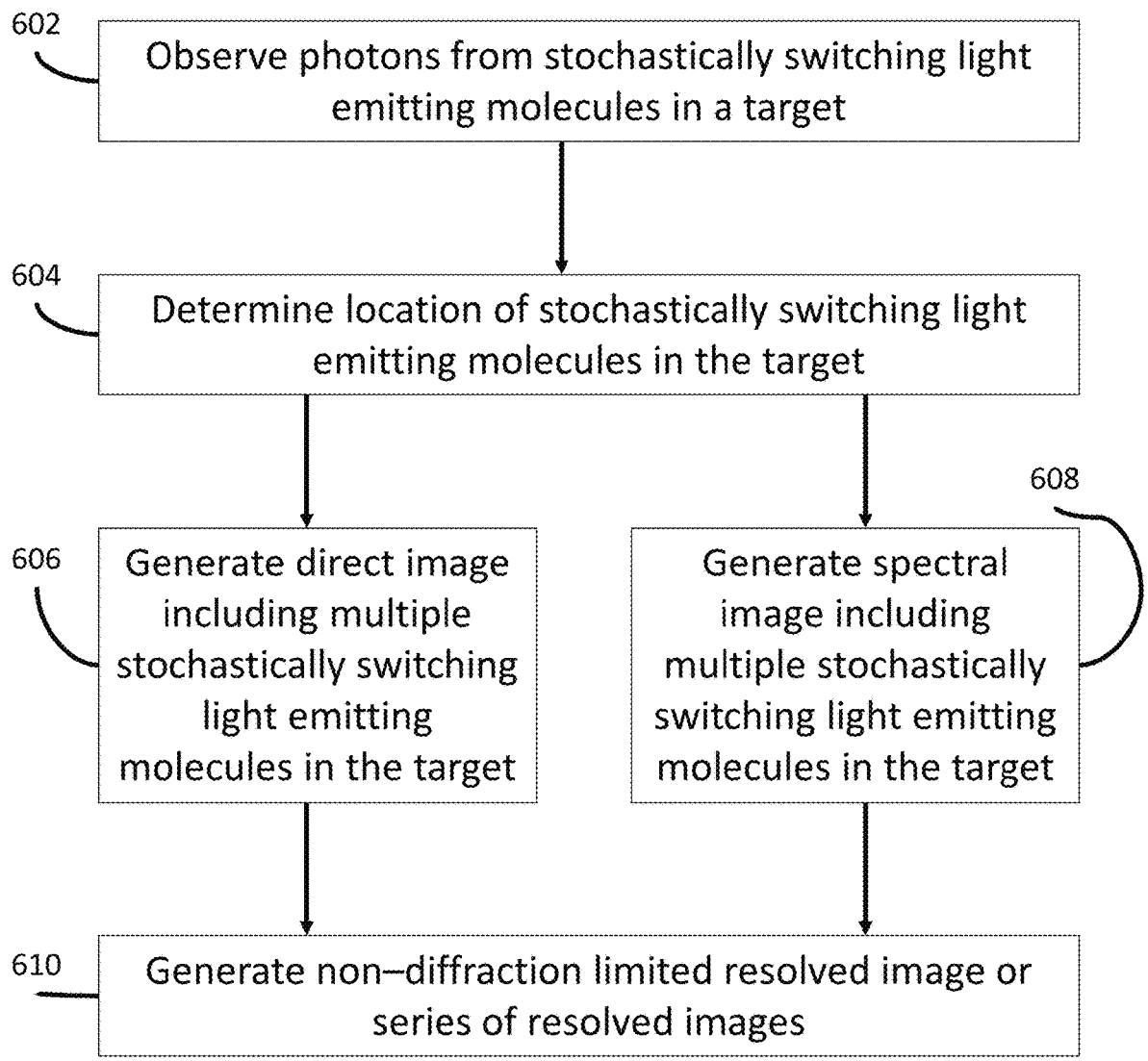
FIG. 6 illustrates a flow diagram of an example method to perform spectroscopic super-resolution microscopic imaging.

FIG. 6 illustrates a flow diagram of an example method 600 to perform spectroscopic super-resolution microscopic imaging. At block 602, photons are observed from stochastically switching light emitting molecules in a target. For example, light emitting molecules are photoswitched or "blinking" after excitation with light from a light source (e.g., a laser, etc.). For example, modest laser illumination is used to excite fluorescent molecules into long-lived dark states and subsequently return them by stochastic photoswitching.

At block 604, location(s) of the stochastically switching light emitting (e.g., "blinking") molecules in the target are determined. For example, a STORM reconstruction algorithm can be used to provide a spatial location for each blinking molecule. These spatial locations can be used as reference points for spectral calibration, for example.

At block 606, a direct image is generating including multiple stochastically switching light emitting molecules in the target. At block 608, a spectral image is generated including the multiple stochastically switching light emitting molecules in the target. For example, a non-dispersed zero-order image and spectrally dispersed first-order spectral image are obtained using a monochromator. By reflecting the zero-order image back to an output port with a sliver mirror, both direct and spectral images can be simultaneously collected by an EMCCD camera.

At block 610, a non-diffraction limited resolved image or series of resolved images is generated. The non-diffraction limited resolve image(s) are formed based on a combination of the direct image and the spectral image including localized stochastically switching light emitting molecules based on the reference spatial locations.

In some examples, by applying spectral regression for nearby blinking localizations, localization precision can be improved by summing of all emitting events from a same molecule. During a period of image acquisition, molecules can be repetitively activated and their emission can be sorted when they match well with each other in both spatial and spectral coordinates (e.g., referred to as spectral regression). Summing of the localization from the same molecule yields a higher photon number, which therefore improves the localization precision (e.g., from ~40 nm to ~10 nm based on a Nyquist criterion).

Figure 7:
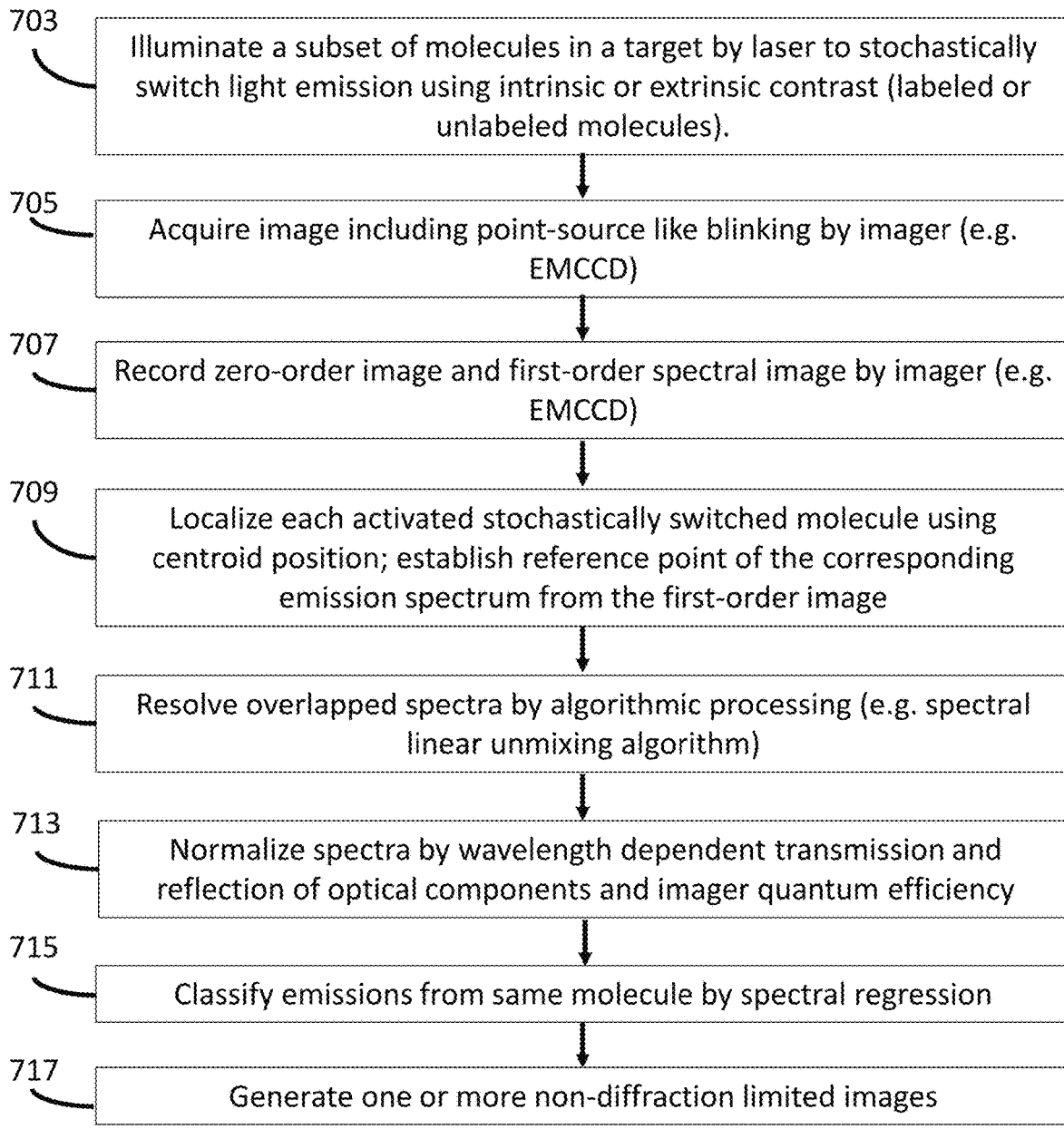
FIG. 7 illustrates a flow diagram of an example method to perform spectroscopic super-resolution microscopic imaging.

FIG. 7 illustrates a flow diagram of another example method 700 to perform spectroscopic super-resolution microscopic imaging. At block 703, a subset of molecules in a target is illuminated by a laser to stochastically switch light emission using intrinsic or extrinsic contrast e.g., (labeled or unlabeled molecules).

At block 705, an image including point-source like blinking is acquired by an imager (e.g., EMCCD). At block 707, a zero-order image and first-order spectral image are recorded by an imager (e.g. EMCCD). For example, a non-dispersed zero-order image and spectrally dispersed first-order spectral image are obtained using a monochromator. By reflecting the zero-order image back to an output port with a sliver mirror, both direct and spectral images can be simultaneously collected by an EMCCD camera.

At block 709, each activated stochastically switched molecule is located using centroid position information, and a reference point of the corresponding emission spectrum is established from the first-order image. For example, centroid positions provide the location of each activated fluorescent molecule and are then used to calibrate the spectral coordinates of the corresponding spectral domain image based on the initial calibration spectrum of the spectrometer.

At block 711, overlapped spectra are resolved by algorithmic processing (e.g. spectral linear unmixing algorithm). For example, molecules that are highly overlapped in their spectra may be difficult to distinguish using conventional multicolor fluorescence microscopy, but slight differences in shape (e.g., differences in emission peak, should peak, etc.) allow for spectral separation of molecules.

At block 713, spectra are normalized by wavelength dependent transmission and reflection of optical components and imager quantum efficiency. At block 715, emissions from a same molecule are classified by spectral regression. In some examples, since a location of each blinking event is unambiguous in the zero-order image, overlapping spectra of near-by fluorophores can be separated with a modified spectral linear unmixing algorithm and associated to each distinct blinking event. By applying spectral linear unmixing and regression, nanoscopic spectral imaging of multi-labeled cells and/or other molecules can be achieved.

At block 717, one or more non-diffraction limited images are generated. The non-diffraction limited resolve image(s) are generated from a location of molecules (taken from the direct image of point-source blinking (acquired at block 705) and spectral data (taken from the spectral image acquired at block 707). Thus, super resolution spectroscopic image is obtained by combining the spatial and spectroscopic information of all localizations using SPLM, for example.

Figure 8:
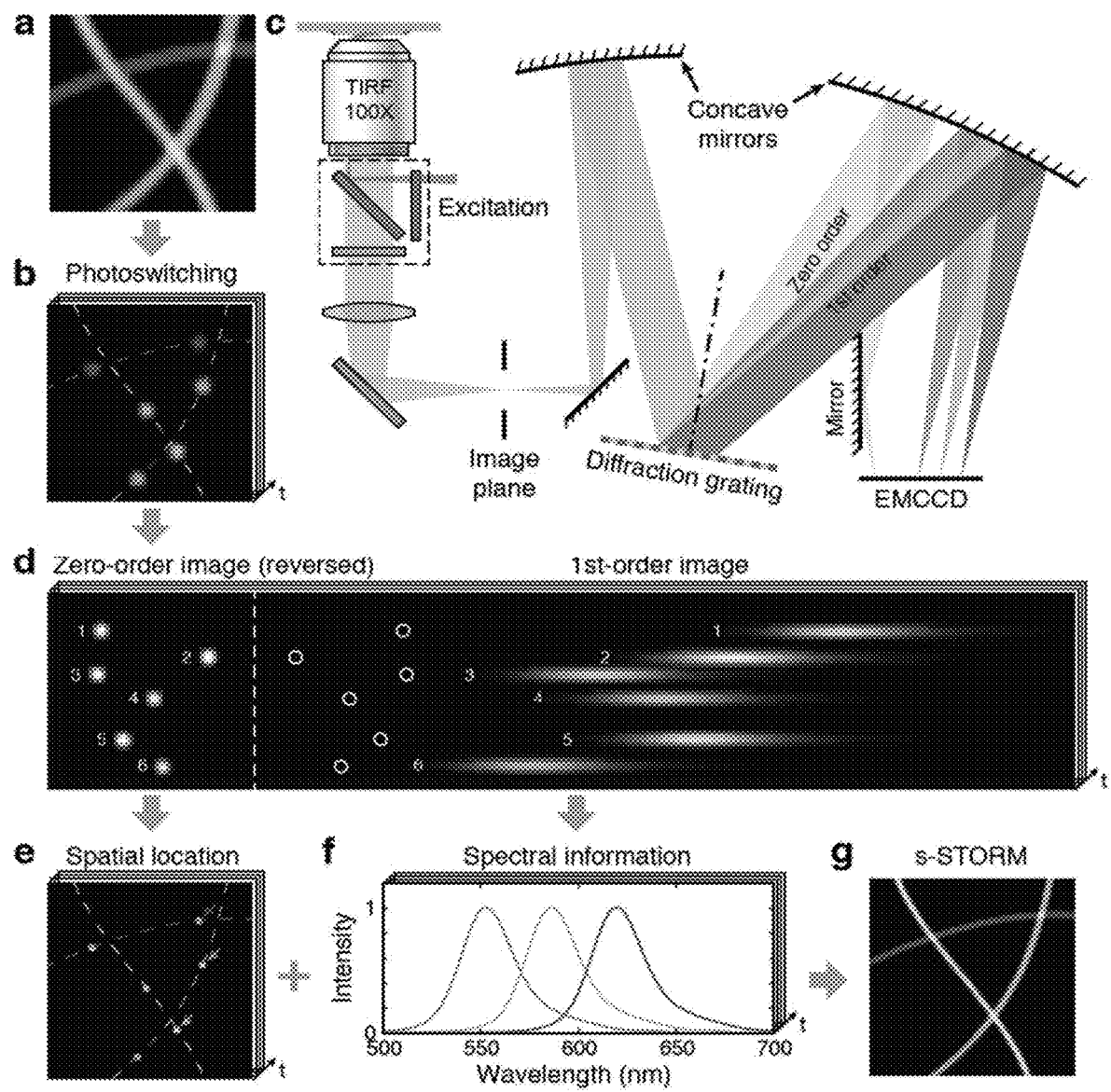
FIGS. 8a-g depict an example spectroscopic super-resolution microscopic imaging configuration and corresponding sequence of image-related actions to generate one or more non-diffraction limited images.

FIGS. 8a-g depict an example spectroscopic super-resolution microscopic imaging configuration and corresponding sequence of image-related actions to generate one or more non-diffraction limited images. FIG. 8c illustrates an example configuration including a total internal reflection fluorescence (TIRF) microscope, an EMCCD, a diffraction grating, and a plurality of mirrors to produce excitation illumination and one or more zero order and first order images.

FIG. 8a depicts a conventional diffraction-limited widefield fluorescence image of a numerical resolution phantom. In FIG. 8b, modest laser illumination is used to turn the fluorophores to long-term dark states and subsequently return them by stochastic photoswitching of the molecules (e.g. photoswitching or "blinking") after excitation with the light of the system in FIG. 8c. The example image of FIG. 8b represents localization of the centroid of sparse emission, which can be used to reconstruct a sub-diffraction-limited image of the sample.

FIG. 8d shows an example image divided into a non-dispersed zero order direct image and a spectrally dispersed first order image generated from the use of one more spectral filtering elements used with any suitable system configuration as described herein (e.g., FIGS. 1, 3, 4, 5, 8c, etc.). For example, a monochromator can be used to obtain the zero and first order images. As shown in the example of FIG. 8c, by reflecting the zero-order image back to the output port with a sliver mirror, an EMCCD can record a time sequence of both zero-order and first-order images with an integration time of 20 ms at 50 frames per second. The correspondence between zero-order and first-order is encoded by numbers reflected in the image. The denoted circles in the image work as their inherent reference points for spectral calibration.

FIG. 8e shows spatial localization of molecules derived from the zero-order image. Localization may be achieved using any suitable single molecule localization techniques as described herein (e.g., using a localization algorithm to determine spatial locations of each blinking). Spectral information, such as the shape, peak, width and other attributes of the spectra curves as shown in FIG. 8f is acquired from the first-order image using any suitable spectroscopic analysis as described herein. FIG. 8f shows representative spectra from three individual blinking events (denoted with arrows in FIG. 8e).

Super resolution spectroscopic images (s-STORM) are obtained by combining the spatial and spectroscopic information of all localizations, as shown in the example of FIG. 8g. In some examples, spatial localization and spectral information are acquired simultaneously or substantially simultaneously to generate the resolved one or more non-diffraction limited images as shown in FIG. 8g.

In some examples, the devices, methods, and systems of the disclosure may us any suitable imager including but not limited to a charge coupled device (CCD), electron multiplying charge coupled device (EMCCD), camera, and complementary metal-oxide-semiconductor (CMOS) imager.

In some examples, the devices, methods, and systems of the disclosure may us any suitable spectral filtering element including but not limited to a dispersive element, transmission grating, grating, band pass filter or prism.

The devices, methods, and systems of the present disclosure may use any light source suitable for spectroscopic super-resolution microscopic imaging, including but not limited to a laser, laser diode, visible light source, ultraviolet light source or infrared light source, superluminescent diodes, continuous wave lasers or ultrashort pulsed lasers.

Generally, the wavelength range of one or more beams of light may range from about 500 nm to about 620 nm. In some examples, the wavelength may range between 200 nm to 600 nm. In some examples, the wavelength may range between 300 to 900 nm. In some examples, the wavelength may range between 500 nm to 1200 nm. In some examples, the wavelength may range between 500 nm to 800 nm. In some examples, the wavelength range of the one or more beams of light may have wavelengths at or around 500 nm, 510 nm, 520 nm, 530 nm, 540 nm, 550 nm, 560 nm, 570 nm, 580 nm, 590 nm, 600 nm, 610 nm, and 620 nm. Generally, the wavelength range of the one or more beams of light may range from 200 nm to 1500 nm. In some examples, the wavelength range of the one or more beams of light may range from 200 nm to 1500 nm. The wavelength range of the one or more beams of light may range from 300 nm to 1500 nm. The wavelength range of the one or more beams of light may range from 400 nm to 1500 nm. The wavelength range of the one or more beams of light may range from 500 nm to 1500 nm. The wavelength range of the one or more beams of light may range from 600 nm to 1500 nm. The wavelength range of the one or more beams of light may range from 700 nm to 1500 nm. The wavelength range of the one or more beams of light may range from 800 nm to 1500 nm. The wavelength range of the one or more beams of light may range from 900 nm to 1500 nm. The wavelength range of the one or more beams of light may range from 1000 nm to 1500 nm. The wavelength range of the one or more beams of light may range from 1100 nm to 1500 nm. The wavelength range of the one or more beams of light may range from 1200 nm to 1500 nm. The wavelength range of the one or more beams of light may range from 1300 nm to 1500 nm. The wavelength range of the one or more beams of light may range from 1300 nm to 1500 nm. In some examples, spectroscopic super-resolution microscopic imaging devices, methods, and systems of the present disclosure include two or more beams of light with wavelengths in the visible light spectrum or the near infrared (NIR) light spectrum. In some examples, spectroscopic super-resolution microscopic imaging includes beams of light with wavelengths in the visible light spectrum, ultraviolet (UV) or the NIR spectrum. Those of skill in the art will appreciate that the wavelength of light may fall within any range bounded by any of these values (e.g. from about 200 nm beam to about 1500 nm).

In some examples, spectroscopic super-resolution microscopic imaging may include multi-band scanning. In some examples, a band may include one or more wavelength ranges containing continuous wavelengths of light within a bounded range. In some examples, a band may include one or more wavelength ranges containing continuous group of wavelengths of light with an upper limit of wavelengths and a lower limit of wavelengths. In some examples, the bounded ranges within a band may include the wavelength ranges described herein. In some examples, spectroscopic super-resolution microscopic imaging may include bands that overlap. In some examples, spectroscopic super-resolution microscopic imaging may include bands that are substantially separated. In some examples, bands may partially overlap. In some examples, spectroscopic super-resolution microscopic may include one or more bands ranging from 1 band to 100 bands. In some examples, the number of bands may include 1-5 bands. In some examples, the number of bands may include 5-10 bands. In some examples, the number of bands may include 10-50 bands. In some examples, the number of bands may include 25-75 bands. In some examples, the number of bands may include 25-100 bands. Those of skill in the art will appreciate that the number of bands of light may fall within any range bounded by any of these values (e.g. from about 1 band to about 100 bands).

In some examples, a frequency of light of one or more beams of light, or bands used in spectroscopic super-resolution microscopic imaging may be chosen based on the absorption-emission bands known for a target. In some examples, a wavelength or wavelengths of light may be chosen such that those wavelengths are within the primary absorption-emission bands known or thought to be known for a particular target.

In some examples, a wavelength or wavelengths of light may be chosen such that those wavelengths are outside the primary absorption-emission bands known or thought to be known for a particular target. For example, although the main absorption bands of polymers such as Poly(methyl methacrylate) (PMMA) and polystyrene (PS) is between 320 nm-400 nm. These polymers may be imaged using spectroscopic super-resolution microscopic imaging in the visible spectrum when excited by a 532-nm continuous wave laser. In some examples, choosing an excitation wavelength outside of the primary or main absorption-emission bands may allow for imaging of stochastic events to generate one or more non-diffraction limited images.

Further, the devices, methods, and systems of the disclosure may allow for various power requirements or laser fluences to generate spectroscopic super-resolution microscopic images. In some examples, a spectroscopic super-resolution microscopic imaging device is configured to illuminate a target with a light source with a fluence from 0.01 kW/cm2 to 100 kW/cm2. In some examples, a spectroscopic super-resolution microscopic imaging device is configured to illuminate a target with a light source fluence of about 5 kW/cm2. In some examples, a spectroscopic super-resolution microscopic imaging device is configured to illuminate a target with a light source with a fluence from 0.01 kW/cm2 to 0.05 kW/cm2. In some examples, a spectroscopic super-resolution microscopic imaging device is configured to illuminate a target with a light source with a fluence from 0.1 kW/cm2 to 0.5 kW/cm2. In some examples, a spectroscopic super-resolution microscopic imaging device is configured to illuminate a target with a light source with a fluence from 0.02 kW/cm2 to 0.8 kW/cm2. In some examples, a spectroscopic super-resolution microscopic imaging device is configured to illuminate a target with a light source with a fluence from 0.2 kW/cm2 to 0.6 kW/cm2. In some examples, a spectroscopic super-resolution microscopic imaging device is configured to illuminate a target with a light source with a fluence from 0.5 kW/cm2 to 1.0 kW/cm2. In some examples, a spectroscopic super-resolution microscopic imaging device is configured to illuminate a target with a light source fluence of about 2 kW/cm2-8 kW/cm2. In some examples, a spectroscopic super-resolution microscopic imaging device is configured to illuminate a target with a light source fluence of about 1 kW/cm2-10 kW/cm2. In some examples, a spectroscopic super-resolution microscopic imaging device is configured to illuminate a target with a light source of about 2 kW/cm2-9 kW/cm2. In some examples, a spectroscopic super-resolution microscopic imaging device is configured to illuminate a target with a light source with a fluence ranging from 3 kW/cm2 to 6 kW/cm2. In some examples, a spectroscopic super-resolution microscopic device is configured to illuminate a target with a light source with a fluence ranging from 2 kW/cm2 to 20 kW/cm2. In some examples, a spectroscopic super-resolution microscopic imaging device is configured to illuminate a target with a light source with a fluence ranging from 5 kW/cm2 to 50 kW/cm2. In some examples, a spectroscopic super-resolution microscopic imaging device is configured to illuminate a target with a light source with a fluence ranging from 10 kW/cm2 to 75 kW/cm2. In some examples, a spectroscopic super-resolution microscopic imaging device is configured to illuminate a target with a light source with a fluence ranging from 50 kW/cm2 to 100 kW/cm2. In some examples, a spectroscopic super-resolution microscopic imaging device is configured to illuminate a target with a light source with a power ranging from 75 kW/cm2 to 100 kW/cm2. In some examples, a spectroscopic super-resolution microscopic imaging device is configured to illuminate a target with a light source with a fluence ranging from 1 kW/cm2 to 40 kW/cm2. Those of skill in the art will appreciate that light source fluence may fall within any range bounded by any of these values (e.g. from about 0.01 kW/cm2 to about 100 kW/cm2).

Figure 9:
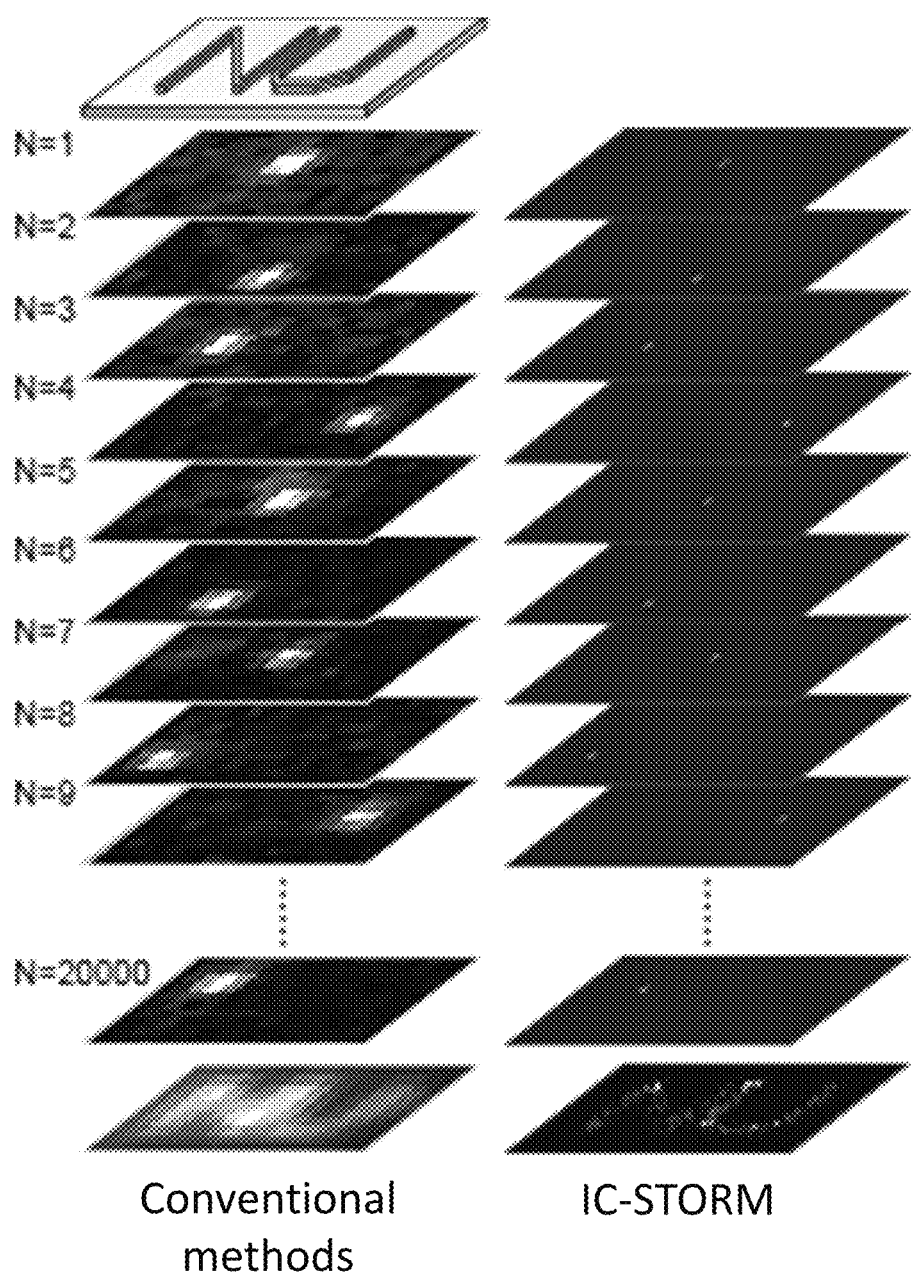
FIG. 9 is a representation of a comparison between conventional methods and IC-STORM including individual observations or imaging of stochastic switching events of one or more moieties or molecules and the processing of photon localization reconstruction for super resolution imaging.

In some examples, spectroscopic super-resolution microscopic may be performed with a range of 1-100,000,000 images generated for resolving one or more one or more non-diffraction limited images. FIG. 9 provides an example indication of n individual images, where single molecules are localized by any suitable single molecule localization methods and the same molecule's spectral information is acquired through any suitable spectroscopic methods. In some examples, n images generated may range from 100-100,000,000. In some examples, n images generated may range from 1000-100,000,000. In some examples, n images generated may range from 1-100,000,000. In some examples, n images generated may range from 100,000-100,000,000. In some examples, n images generated may range from 1,000,000-100,000,000. In some examples, n images generated may range from 10,000,000-100,000,000. In some examples, n images generated may range from 1-100,000. In some examples, n images generated may range from 1-20,000. In some examples, n images generated may range from 1,000-10,000. In some examples, n images generated may range from 50,000-100,000. In some examples, n images generated may range from 100,000-5,000,000. In some examples, n images generated may range from 1,000,000-100,000,000. In some examples, n images generated may range from 10,000,000-50,00,000. In some examples, n images generated may be at least about 1, 1000, 10,000, 20,000, 50,000, 100,0000, 1,000,000, 10,000,000, or 100,000,000. In some examples, n images generated may be at most about 1, 1000, 10,000, 20,000, 50,000, 100,0000, 1,000,000, 10,000,000, or 100,000,000. Those of skill in the art will appreciate that n images generated may range from 1-100,000,000 images.

D. Single Molecule Localization

The devices, methods, and systems of the disclosure provide for capturing one or more images of the light and localizing the light-emitting particles using one or more single molecule microscopic methods. In some examples, a spectral filtering element, such as a diffraction grating or band pass filter may allow the generation of zero-order and first-order images for further analysis. Zero-order images may be used to determine the probabilistic locations of the light-emitting molecules from their localized point spread functions.

Generally, single molecule localization comprises selecting emission spots in a desired wavelength range corresponding to light-emitting molecules. In some examples, there may be a single emission wavelength range. In alternative examples, there may be two or more wavelength ranges. Single molecule localization may include only identifying and processing in focus spots, whether or not they are centered on expected illumination positions. In particular, by suitable selection of in focus spots, significant improvements in axial resolution can be achieved. Emission spots may be identified using any suitable localization method including but not limited to those adapted for use with stochastic imaging approaches such as stochastic optical reconstruction microscopy, spectral precision distance microscopy (SPDM), spectral precision distance microscopy with physically modifiable fluorophores (SPDMphymod), photo activated localization microscopy (PALM), photo-activation localization microscopy (FPALM), photon localization microscopy (PLM), direct stochastical optical reconstruction microscopy (dSTORM), super-resolution optical fluctuation imaging (SOFI), and 3D light microscopical nanosizing microscopy (LIMON). In some examples, single molecule localization methods may also include methods derived for particle tracking.

In some examples, single molecule localization methods may be chosen based on the density of the spacing of the data obtained. In some examples, emission spots may be located through the method of iteratively fitting multiple point spread functions (PSFs) to regions of image data which appear to contain overlapping signals. In other examples, the emission spots may be located using compressed sensing. An example of compressed sensing includes: extracting emission spot co-ordinates from potentially overlapping image data by first calculating the expected image from each possible emission spot position; and determining the emission spot positions that give rise to real signals in light of this complete prior knowledge. Emission spots may be located using Bayesian Localization Microscopy, which optimizes a model of fluorophore density to fit the fluorescence measurements made in a whole series of images. In some examples, spots may be identified using a generalized likelihood ratio test (GLRT) segmentation method based on spot diameter and signal to noise ratio. The GLRT threshold may be adjusted iteratively, for example.

In some examples, emission spots may be identified if their diameters match the diameter of the expected PSF of the collection optics. The expected PSF may be calculated or may be determined by experiment. Spots may be determined to have diameters that match the expected PSF if they are equal to the expected diameter or vary from the expected diameter by less than a threshold value. The threshold value may be based on the expected standard deviation of the PSF. The threshold value may be adjusted iteratively. Identification of emission spots may further include selecting an axial focus of the images by suitably selecting the PSF diameter and/or threshold value.

The centroid of each identified spot may be located using any suitable method including but not limited to those used for particle localization and tracking and stochastic imaging approaches such as PALM/STORM and SOFI and other described herein. In some examples, each identified spot may be determined by using nonlinear curve fitting of a symmetric Gaussian function with a fixed standard deviation. The standard deviation value may be fixed based on estimation or may be fixed based on an average value determined from identified spots. Enhancing each image or sub images may be carried out by any suitable technique including but not limited to those developed for PALM, STORM and SOFI and other described herein. In some examples, enhancement is carried out using a Gaussian mask. The Gaussian mask may have a fixed or user defined standard deviation. Enhancement may additionally or alternatively include scaling the sub image. In some examples, a scale factor of the order 2 may be applied to the sub image.

In some examples, a composite image is generated from a sequence of enhanced images. A composite image may be generated by calculating a 2D histogram of the emission spot positions with a chosen square bin size, which may correspond to the pixel size of the composite image. This may then be displayed as a pixelated image whose local intensity is proportional to the bin occupancy. In some examples, the composite image may be formed with a Quad-Tree Based Adaptive Histogram based on a quad-tree representation of the localization data. In other examples, the composite image may be formed using a triangulation technique such as Delaunay Triangulation Based Visualization, for example. Subsequent processing including deconvolution approaches including but not limited to Lucy-Richardson deconvolution may also be applied. Determining the centroid positions of the one or more localized activated light-emitting molecules may allow establishing a reference point of the corresponding emission spectrum of one or more localized activated light-emitting molecules.

E. Spectroscopic Methods and Analysis i. Spectral Unmixing

The devices, methods, and systems of the disclosure provide for one or more spectroscopic analyses of the corresponding emission spectrum of the one or more localized activated light-emitting molecules. As described herein, the emission spectra for each light-emitting molecule may be captured with a spectrometer via methods known in the art related to Raman spectroscopy, optical fluorescence microscopy, infrared spectroscopy, ultraviolet spectroscopy, laser microscopy and confocal microscopy.

Generally, a first-order image, generated through the use of a spectral filtering element, such as a diffraction element or prism, allows individual spectra to be captured associated with each corresponding reference point for each emission spot of individual light-emitting molecules.

In some examples, the zero-order image and first order image are generated simultaneously. In some examples, the zero-order image and first order image, localization information about individual emission spots of individual light-emitting molecules, and spectra information are and generated and captured simultaneously.

When data at multiple wavelengths are obtained, however, it is possible to improve the contrast and detection sensitivity by spectral unmixing (e.g., by resolving the spectral signature of the absorption of the light-emitting molecules to be imaged over other non-specific spectral contributions, or from confounding signals from molecules with overlapping spectral signatures). In some examples, other types of light scattering or signals from non specific absorption (e.g. hemoglobin, or DNA), Raman scattering may be removed using spectral unmixing.

Spectral unmixing methods based on differential or fitting algorithms use known spectral information to process the image on a pixel-by-pixel basis. These methods try to find the source component (e.g., a distribution of a certain light-emitting molecule's emission) that best fits its known absorption spectrum in the least-squares sense.

There are numerous algorithmic methods for spectra unmixing known in the art. Generally, given the (n×m) multispectral measurement matrix M, where n is the number of image pixels and m is the number of measurements, as well as the (k×m) spectral matrix S with the absorption coefficients of the k components at the m measurement wavelengths, the data can be unmixed via $R_{pinv}=MS^+$, where $S^+$ is the Moore-Penrose pseudoinverse of S and $R_{pinv}$ is the reconstructed spatial distribution (image) of the chromophore of interest.

In some examples, separation requires other unmixing methods or algorithms when the exact spectral profile of the background contribution is not always known, or the spectral signatures or profiles between adjacent localized light-emitting molecules are very similar (e.g., in in-vivo imaging, use of extrinsic labels with highly similar spectral signatures etc.). In addition, the spectral signature of the agent of interest may also be not accurately known, for instance the absorption spectrum may change in different biochemical environments.

In some examples, spectral unmixing can be tackled by the use of multivariate data analysis and matrix factorization algorithms, such as principal component analysis (PCA), non-negative matrix factorization (NNMF), multivariate curve resolution (MCR) or independent component analysis (ICA). Principal Component Analysis is a blind source unmixing technique that is based on the assumption that the source components are statistically uncorrelated. PCA yields a linear orthogonal transformation into a new coordinate system, in which the largest data variance is projected onto the first principal component, the largest remaining variance onto the second one, and so on. Consequently, the correlated measurement data is unmixed by being transformed to uncorrelated principal components.

PCA can be calculated as a singular value decomposition of M or as an eigenvalue decomposition of its covariance matrix (e.g., RPCA=UTPCAM, where U is a transformation matrix that represents absorption spectra of the calculated principal components).

Independent Component Analysis (ICA) is yet another blind source separation technique, but it is based on a different assumption about the sources than PCA. While the latter assumes uncorrelated sources, ICA finds end members that satisfy the more general and therefore stronger condition of statistical independence. The ICA algorithm seeks a transformation of the dependent mixed spectral components into a set of independent source components and also yields the corresponding mixing matrix UICA. Contrary to the pixel-by-pixel processing approach in the differential and fitting unmixing methods, the key element in multivariate approaches is the unaided identification of changes that are common across various pixels, helping to identify contrast agents that have a non-uniform spatial biodistribution.

Generally, any suitable spectral unmixing algorithm or combination of algorithms may be used to resolve individual spectral signatures. Attributes of individual spectral signatures, including peak, size, shape, width, etc., may be used in one or more spectral unmixing methods or algorithms with the devices, methods, and systems of the disclosure.

In some examples, stochastic blinking events occurring along the same horizontal position within the same frame can cause spectral overlap, which is highly probable in regions with many fluorophores in close proximity. Since the locations of blinking events are unambiguous in the direct image and the spectra from different blinking events are linearly mixed in the spectral image, overlapping can thus be separated with a modified spectral linear unmixing algorithm. If we have n spectra from same type of dye molecule with emission spectrum s, and the ith spectrum $s(x_i)$ emitted at $x_i$ position with intensity of $a_i$ the observed spectrum S can be expressed as $$S = \sum_{i=1}^{n} a_i \, s(x_i) + w,$$

where w is an error term accounting for additive noise (such as sensor noise and model inadequacies). Least squares fitting may be applied to conduct linear unmixing and separate overlap in spectral domain. By using positions of two bright spots as inherent reference points, spectra from their pixel coordinates can be further calibrated. Finally, spectra may be divided by the wavelength dependent system efficiency to recover the actual emission spectra.

Acquiring accurate reference spectra may be essential in generating satisfactory linear unmixing results. Although the spectral profiles of synthetic dyes and fluorescent proteins are accurately known, they are usually measured from molecule assembles with spectral broadening due to underlying conformational heterogeneity. To obtain the reference spectra for SPLM the fluorescence spectrum was measured from single molecule emission in the absence of inhomogeneous broadening. It can be obtained from frames with sparse single-molecule events. For single molecule spectroscopy, the spectral shift $\lambda_i$ nay be considered which may be from underlying conformational heterogeneity. The observed spectrum S can be further expressed as $$S = \sum_{i=1}^{n} a_i \, s(x_i + \lambda_i) + w.$$

ii. Normalization, Spectral Regression for Classification of Molecule Emissions

Resolving individual spectral signatures in combination with emission spot localization of individual light-emitting molecules may allow for improved resolution. Individual spectral signatures can be resolved or distinguished for each localized emission spot for individual light-emitting molecules. In some examples, individual spectral signatures for 2 or more different molecules with the same absorption-emission band properties may be resolved. In some examples, individual spectral signatures for 2 or more different molecules with the same type of extrinsic label (e.g., both molecules may be labeled with rhodamine) may be resolved. In some examples, individual spectral signatures for 2 or more different molecules with 2 or more different types of extrinsic labels (e.g. molecules in a population may be labeled with many different extrinsic labels such as DAPI, rhodamine, GFP, RFP, YFP etc.) may be resolved.

The spatial and spectral resolution of the reported spectroscopic super-resolution imaging methods may be dependent on the number of photons being collected from each fluorescent molecule, which is ultimately determined by the irreversible photo-bleaching threshold. Additionally, the background signals, such as auto-fluorescence, Raman, and Rayleigh scattering from the sample, may also need to be considered in order to achieve the optimal spatial and spectral resolution.

In some examples, various filtering, normalization and calibration steps may be used in conjunction with the devices, methods, and systems of the present disclosure. For example, the dispersion of the imaging system may be calibrated prior to the image acquisition and factored into subsequent image reconstructions. Background signals may be removed by subtracting the average of adjacent image frames without the presence of stochastic emission. The spectrum of one or more individual emission spots may be further normalized by the wavelength dependent transmission and reflection of optical components and the camera quantum efficiency.

In some examples, where there may be spectral overlap or additional methods may be required to resolve confounding signals due to overlapped spectra signatures from one or more molecules, during the period of image acquisition, molecules can be repetitively activated and their emission can be sorted when there is a reasonable match in both spatial and spectral coordinate. This process may be referred to as spectral regression.

Using the emission spectrum to discern the labels constitutes a methodical advancement over the sequential recording used in earlier multicolor experiments. As compared to previous multichannel approaches, spectroscopic super-resolution microscopic imaging of the present disclosure may bring important advantages. For example, multiple fluorophores can be excited by the same illumination without additional imaging filters. Simultaneous fluorophore characterization may improve the imaging speed and largely extends the combination of markers discernible in multi-stained samples. In practical applications, high spectral resolution may not be required to identify the vast majority of fluorescent molecules. A low dispersion version of SPLM (e.g., using lower groove density of the grating or shorter monochromator focal length) can improve the signal to noise ratio since the available photons from each single molecule emission occupies less pixels in the spectral image. A low dispersion version of SPLM can also reduce overlapping and thus increase the throughput—namely, the number of spectra that can be distinguished in one frame. This sequentially accelerates the image recording, thereby minimizing sample drift during acquisition. On the other hand, high dispersion version can be realized for identifying high resolution spectral signals (e.g., super-resolution imaging using the blinking of single-molecule surface enhanced Raman scattering).

iii. Photobleaching and Oxidation

In some examples, one or more solvents or additives may be applied to the sample to affect the rate or amount of photobleaching of the sample. In some examples, oxygen scavengers may be applied to a sample to reduce the amount or rate of photobleaching. In some examples, non limiting examples of solvents that may be applied to the sample include water, oil, mineral oil, PEG, glycol, DTT, or enzymes such as glucose oxidase. Any agent suitable to reduce photobleaching of a sample may be used.

F. Image Processing

Various image-processing techniques may also be used to facilitate determination of the entities. For example, drift correction or noise filters may be used. Generally, in drift correction, a fixed point is identified (for instance, as a fiduciary marker, such as a fluorescent particle immobilized to a substrate), and movements of the fixed point (e.g., due to mechanical drift) are used to correct the determined positions of the switchable entities. In another example method for drift correction, a correlation function between images acquired in different imaging frames or activation frames can be calculated and used for drift correction. In some examples, the drift may be less than about 1000 nm/min, less than about 500 nm/min, less than about 300 nm/min, less than about 100 nm/min, less than about 50 nm/min, less than about 30 nm/min, less than about 20 nm/min, less than about 10 nm/min, or less than 5 nm/min. Such drift may be achieved, for example, in a microscope having a translation stage mounted for x-y positioning of the sample slide with respect to the microscope objective. The slide may be immobilized with respect to the translation stage using a suitable restraining mechanism (e.g., spring loaded clips, etc.). In addition, a buffer layer may be mounted between the stage and the microscope slide. The buffer layer may further restrain drift of the slide with respect to the translation stage, for example, by preventing slippage of the slide in some fashion. The buffer layer, in one example, is a rubber or polymeric film, for instance, a silicone rubber film.

Accordingly, one example of the invention is directed to a device comprising a translation stage, a restraining mechanism (e.g., a spring loaded clip) attached to the translation stage able to immobilize a slide, and optionally, a buffer layer (e.g., a silicone rubber film) positioned such that a slide restrained by the restraining mechanism contacts the buffer layer. To stabilize the microscope focus during data acquisition, a "focus lock" device may be used in some cases. As a non-limiting example, to achieve focus lock, a laser beam may be reflected from the substrate holding the sample and the reflected light may be directed onto a position-sensitive detector, for example, a quadrant photodiode. In some cases, the position of the reflected laser, which may be sensitive to the distance between the substrate and the objective, may be fed back to a z-positioning stage (e.g., a piezoelectric stage) to correct for focus drift.

Another aspect of the present disclosure is directed to computer-implemented methods. For instance, a computer and/or an automated system may be provided that is able to automatically and/or repetitively perform any of the methods described herein. As used herein, "automated" devices refer to devices that are able to operate without human direction (e.g., an automated device can perform a function during a period of time after a human has finished taking any action to promote the function such as by entering instructions into a computer). Typically, automated equipment can perform repetitive functions after this point in time. Processing instructions may also be recorded onto a machine-readable medium in some cases.

In some examples, a computer may be used to control excitation of the switchable entities and the acquisition of images of the switchable entities. In one set of examples, a sample may be excited using light having various wavelengths and/or intensities, and the sequence of the wavelengths of light used to excite the sample may be correlated, using a computer, to the images acquired of the sample containing the switchable entities. For instance, the computer may apply light having various wavelengths and/or intensities to a sample to yield different average numbers of activated switchable elements in each region of interest (e.g., one activated entity per location, two activated entities per location, etc.). In some examples, this information may be used to construct an image of the switchable entities, in some cases at sub-diffraction limit resolutions, as noted above.

Still other examples of the present disclosure are generally directed to a system able to perform one or more of the examples described herein. For example, the system may include a microscope, a device for activating and/or switching the entities to produce light having a desired wavelength (e.g., a laser or other light source), a device for determining the light emitted by the entities (e.g., a camera, which may include color-filtering devices, such as optical filters), and a computer for determining the spatial positions of the two or more entities.

III. Software and Computer Systems for Spectroscopic Super-Resolution Microscopic Imaging In various examples, certain methods and systems may further include software programs on computer systems and use thereof. Accordingly, computerized control for the synchronization of system functions such as laser system operation, fluid control function, and/or data acquisition steps are within the bounds of the invention. The computer systems may be programmed to control the timing and coordination of delivery of sample to a detection system, and to control mechanisms for diverting selected samples into a different flow path. In some examples, the computer may also be programmed to store the data received from a detection system and/or process the data for subsequent analysis and display.

Figure 19:
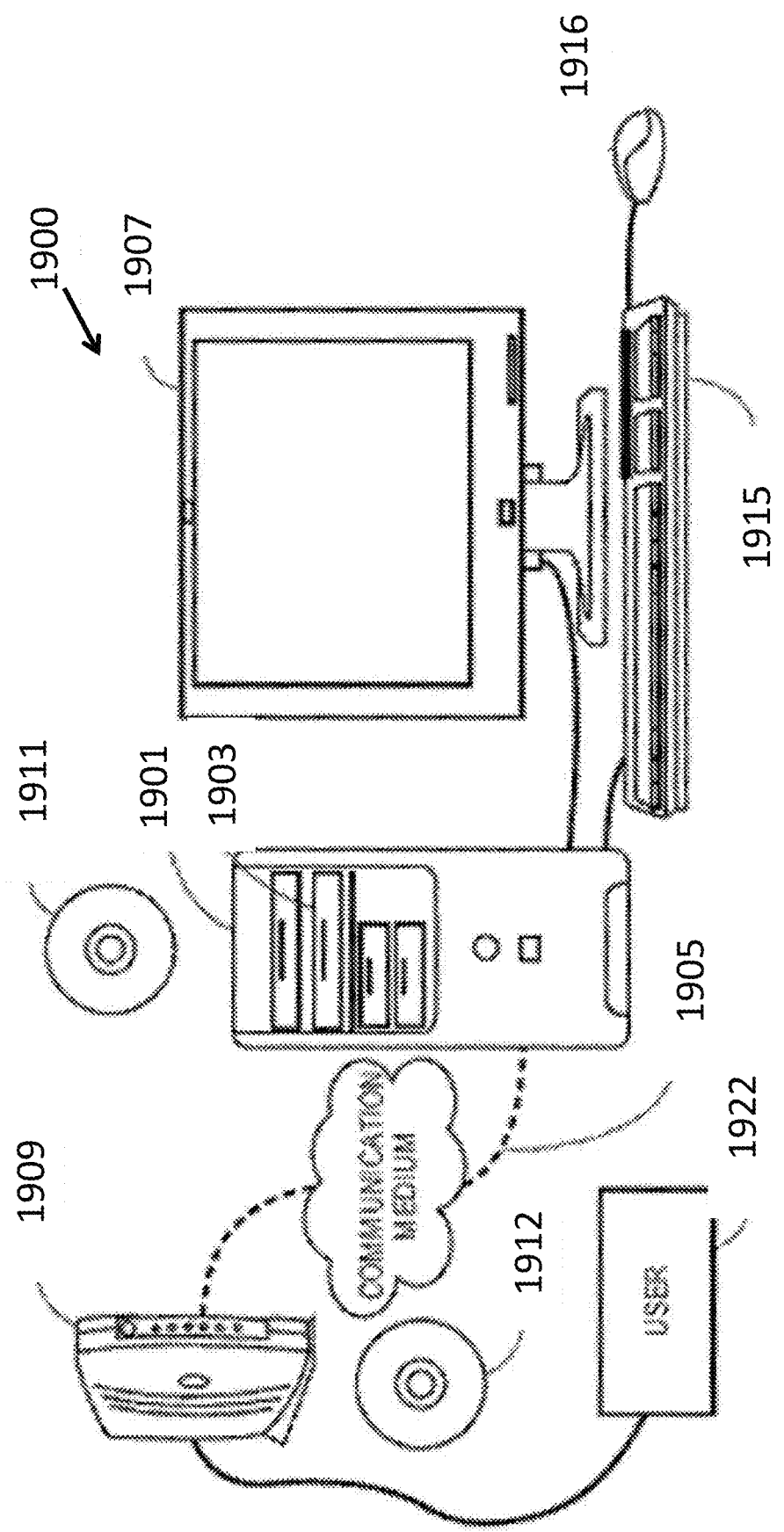
FIG. 19 is an example schematic diagram of a computing system suitable for use with the devices, methods, and systems of the disclosure.

The computer system 1900 illustrated in FIG. 19 may be understood as a logical apparatus that can read instructions from media 1911 and/or a network port 1905, which can optionally be connected to server 1909 having fixed media 1912. The system, such as shown in FIG. 19 can include a CPU 2001, disk drives 1903, optional input devices such as keyboard 1915 and/or mouse 1916 and optional monitor 1907. Data communication can be achieved through the indicated communication medium to a server at a local or a remote location. The communication medium can include any mechanism for transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 1922 as illustrated in FIG. 19.

Figure 20:
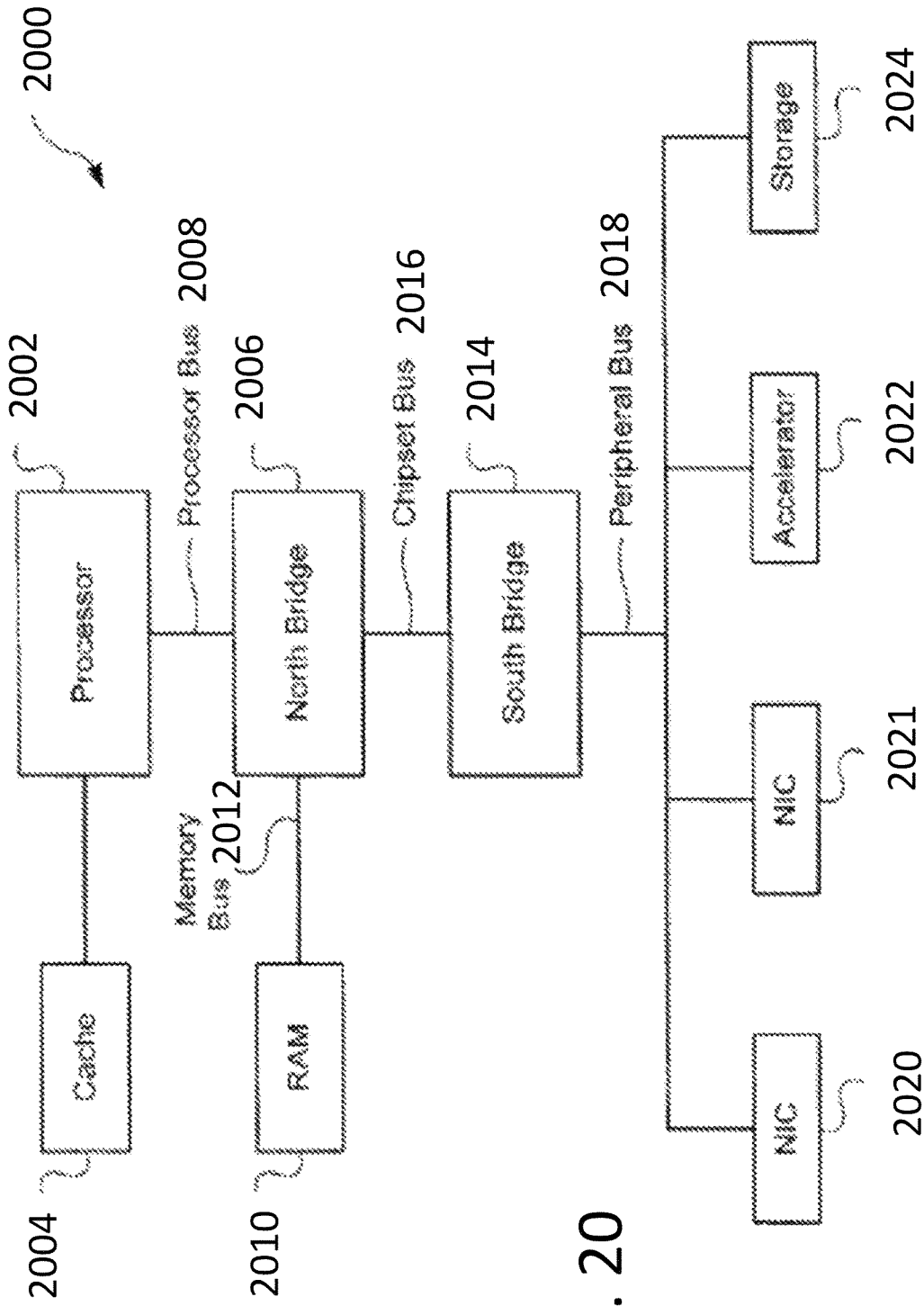
FIG. 20 is a block diagram illustrating a first example architecture of a computer system that can be used in connection with a spectroscopic super-resolution microscopic imaging device.

FIG. 20 is a block diagram illustrating a first example architecture of a computer system 2000 that can be used in connection with examples of the present disclosure. As depicted in FIG. 20, the example computer system can include a processor 2002 for processing instructions. Non-limiting examples of processors include: Intel Xeon™ processor, AMD Opteron™ processor, Samsung 32-bit RISC ARM 1176JZ(F)-S v1.OTM processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some examples, multiple processors or processors with multiple cores can also be used, whether in a single computer system, in a cluster, or distributed across systems over a network comprising a plurality of computers, cell phones, and/or personal data assistant devices.

As illustrated in FIG. 20, a high speed cache 2004 can be connected to, or incorporated in, the processor 2002 to provide a high speed memory for instructions or data that have been recently, or are frequently, used by processor 2002. The processor 2002 is connected to a north bridge 2006 by a processor bus 2008. The north bridge 2006 is connected to random access memory (RAM) 2010 by a memory bus 2012 and manages access to the RAM 2010 by the processor 2002. The north bridge 2006 is also connected to a south bridge 2014 by a chipset bus 2016. The south bridge 2014 is, in turn, connected to a peripheral bus 2018. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 2018. In some alternative architectures, the functionality of the north bridge can be incorporated into the processor instead of using a separate north bridge chip.

In some examples, system 2000 can include an accelerator card 2022 attached to the peripheral bus 2018. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 2024 and can be loaded into RAM 2010 and/or cache 2004 for use by the processor. The system 2000 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with examples of the presently disclosed technology.

In this example, system 2000 also includes network interface cards (NICs) 2020 and 2021 connected to the peripheral bus for providing network interfaces to external storage, such as Network Attached Storage (NAS) and other computer systems that can be used for distributed parallel processing.

Figure 21:
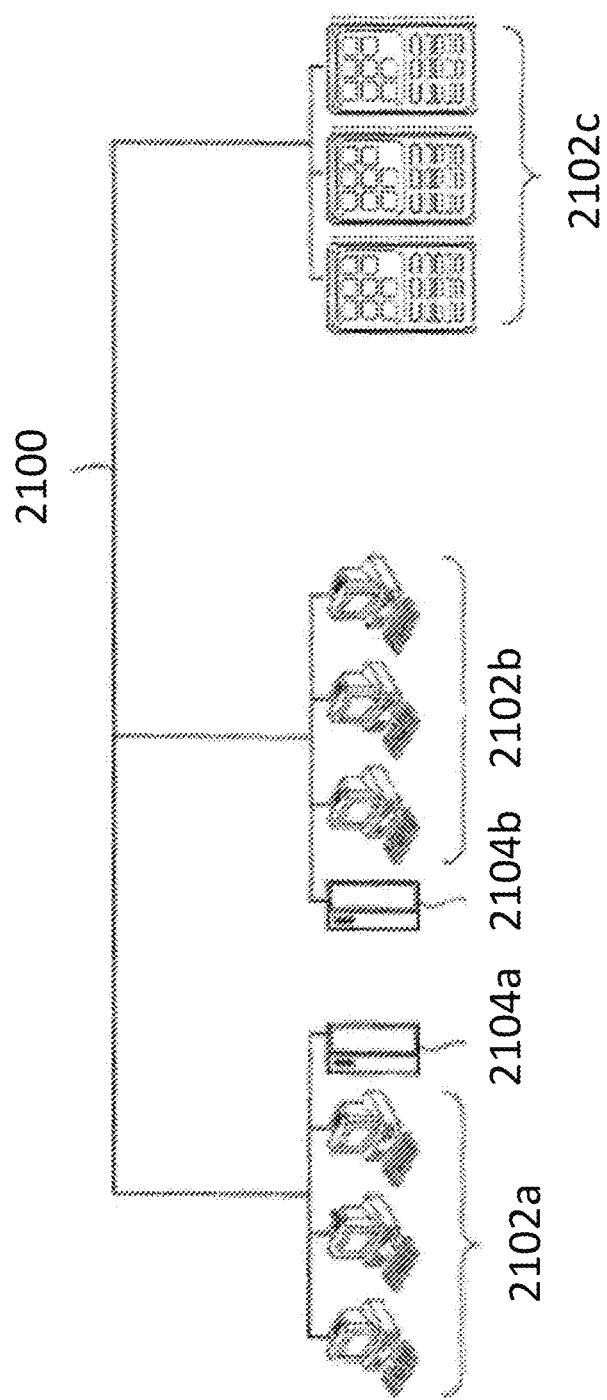
FIG. 21 is a diagram showing an example network with a plurality of computer systems, and a plurality of cell phones and personal data assistants configured with a spectroscopic super-resolution microscopic imaging device.

FIG. 21 is a diagram showing a network 2100 with a plurality of computer systems 2102*a* and 2102*b*, a plurality of cell phones and personal data assistants 2012*c*, and Network Attached Storage (NAS) 2014*a* and 2104*b*. In some examples, systems 2102*a*, 2102*b*, and 2102*c* can manage data storage and optimize data access for data stored in Network Attached Storage (NAS) 2104*a* and 2104*b*. A mathematical model can be used for the data and be evaluated using distributed parallel processing across computer systems 2102*a*, and 2102*b*, and cell phone and personal data assistant systems 2102*c*. Computer systems 2102*a*, and 2102*b*, and cell phone and personal data assistant systems 2102*c* can also provide parallel processing for adaptive data restructuring of the data stored in Network Attached Storage (NAS) 2104*a* and 2104*b*. FIG. 21 illustrates an example only, and a wide variety of other computer architectures and systems can be used in conjunction with the various examples of the presently disclosed technology. For example, a blade server can be used to provide parallel processing. Processor blades can be connected through a back plane to provide parallel processing. Storage can also be connected to the back plane or as Network Attached Storage (NAS) through a separate network interface.

In some examples, processors can maintain separate memory spaces and transmit data through network interfaces, back plane or other connectors for parallel processing by other processors. In other examples, some or all of the processors can use a shared virtual address memory space.

Figure 22:
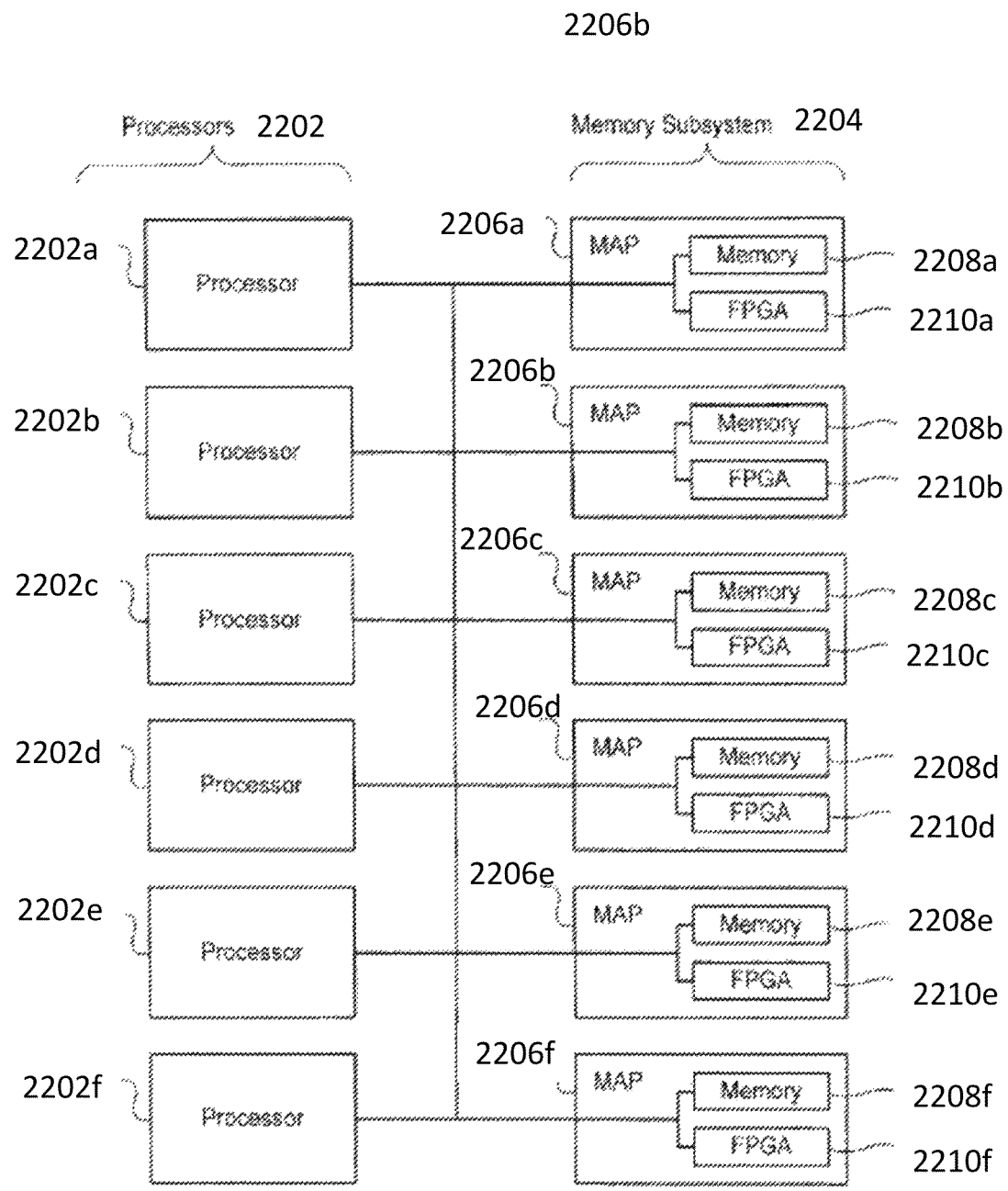
FIG. 22 is a block diagram of an example multiprocessor computer system configured with a spectroscopic super-resolution microscopic imaging device.

FIG. 22 is a block diagram of a multiprocessor computer system 2202 using a shared virtual address memory space in accordance with an example imaging device. The system includes a plurality of processors 2202*a-f* that can access a shared memory subsystem 2204. The system incorporates a plurality of programmable hardware memory algorithm processors (MAPs) 2206*a-f* in the memory subsystem 2204. Each MAP 2206*a-f* can comprise a memory 2208*a-f* and one or more field programmable gate arrays (FPGAs) 2210*a-f*. The MAP 2206*a-f* provides a configurable functional unit and particular algorithms or portions of algorithms can be provided to the FPGAs 2210*a-f* for processing in close coordination with a respective processor. For example, the MAPs 2206*a-f* can be used to evaluate algebraic expressions regarding the data model and to perform adaptive data restructuring in certain examples. In this example, each MAP 2206*a-f* is globally accessible by all of the processors for these purposes. In one configuration, each MAP can use Direct Memory Access (DMA) to access an associated memory 2208*a-f*, allowing it to execute tasks independently of, and asynchronously from, the respective microprocessor 2202*a-f*. In this configuration, a MAP 2206*a-f* can feed results directly to another MAP 2206*a-f* for pipelining and parallel execution of algorithms.

The above computer architectures and systems are examples only, and a wide variety of other computer, cell phone, and personal data assistant architectures and systems can be used in connection with certain examples, including systems using any combination of general processors, co-processors, FPGAs and other programmable logic devices, system on chips (SOCs), application specific integrated circuits (ASICs), and other processing and logic elements. In some examples, all or part of the computer system can be implemented in software or hardware. Any variety of data storage media can be used in connection with certain examples, including random access memory, hard drives, flash memory, tape drives, disk arrays, Network Attached Storage (NAS) and other local or distributed data storage devices and systems.

In some examples, the computer system can be implemented using software modules executing on any of the above or other computer architectures and systems. In other examples, the functions of the system can be implemented partially or completely in firmware, programmable logic devices such as field programmable gate arrays (FPGAs) as referenced in FIG. 22, system on chips (SOCs), application specific integrated circuits (ASICs), or other processing and logic elements. For example, the Set Processor and Optimizer can be implemented with hardware acceleration through the use of a hardware accelerator card, such as accelerator card 2022 illustrated in FIG. 20.

VI. Terminology

The terminology used therein is for the purpose of describing particular examples only and is not intended to be limiting of a device of this disclosure. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Several aspects of a device of this disclosure are described above with reference to example applications for illustration. It should be understood that numerous specific details, relationships, and methods are set forth to provide a full understanding of a device. One having ordinary skill in the relevant art, however, will readily recognize that a device can be practiced without one or more of the specific details or with other methods. This disclosure is not limited by the illustrated ordering of acts or events, as some acts may occur in different orders and/or concurrently with other acts or events. Furthermore, not all illustrated acts or events are required to implement a methodology in accordance with this disclosure.

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another example. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

EXAMPLES

Example 1

Figure 10:
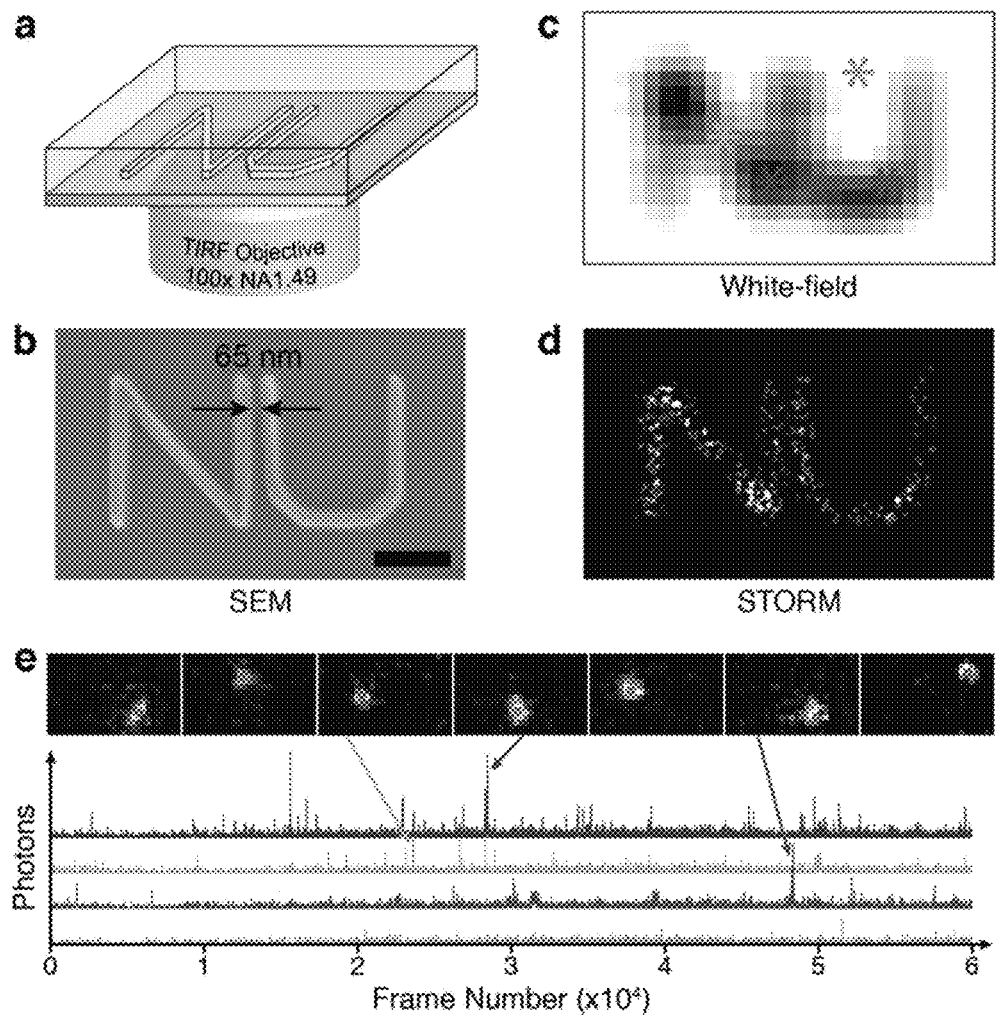
FIGS. 10a-e represent an example fabricated pattern and associated image analysis.

As shown in FIG. 10a, a common lithographic polymer, PMMA was used to create a nanopattern sample on glass substrate, and then used the sample to confirm the source of the stochastic radiation. FIG. 10b shows a scanning electron microscopy (SEM) image of an "NU" logo pattern fabricated using E-Beam lithography with a 100 nm linewidth in a 200 nm-thick PMMA film. The 65 nm wide gap between the letters (highlighted in FIG. 10b) cannot be resolved using optical white-field microscopy (FIG. 10c), because the features size is well below the maximum diffraction-limited resolution of 225 nm using a 1.49-NA TIRF objective. A 532-nm laser was used to excite the sample, revealing stochastic radiation events. Images were reconstructed that localized stochastic radiation using STORM (FIG. 10d). Multiple locations of the glass substrate with and without PMMA coating were observed. Interestingly, stochastic blinking events were observed from the "NU" pattern (FIG. 10e) under modest laser powers at an average rate of 0.0072 events per $\mu m^2$.

To understand the type of radiation generating the blinking events, spectroscopy experiments were conducted using our custom-built STORM microscope with a secondary light path for SMFS. The 200 nm-thick PMMA film sample was excited using a 532 nm incident beam at fluences ranging from 1-10 $kW/cm^2$. Spectra were acquired using a high-speed electron-multiplied CCD (EMCCD) (ProEM512, Princeton) attached to a spectrometer (SP2150i, Princeton) with a 1 nm spectral resolution. Individual blinking events can be isolated by using a narrow spectrometer entrance slit and noting the vertical position of the stochastic signal on the EMCCD detector array. The spectra of stochastic radiation from both types of blinking events were recorded from 200 consecutive frames with an integration time of 100 ms per frame. All spectral blinking events observed over 10 minutes were summed to determine the average spectral characteristics of the blinking.

Figure 11:
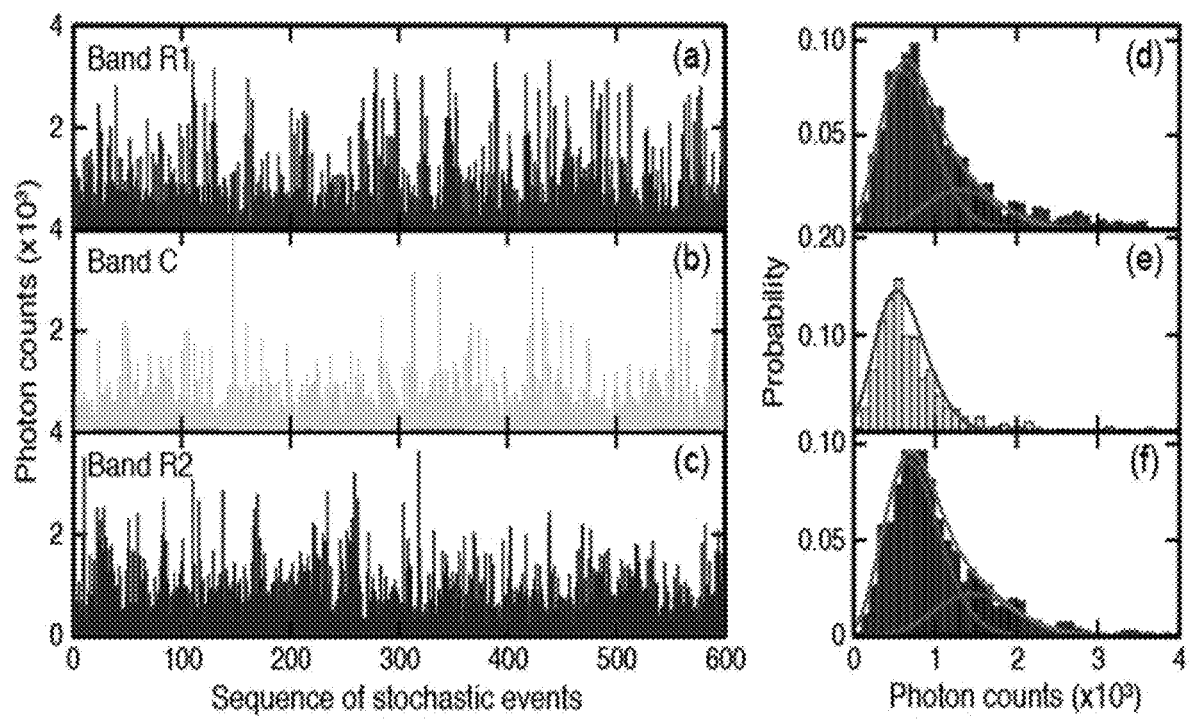
FIGS. 11a-f show example time traces of the fluorescence intensity and spectra affirmed short- and long-lived blinking lifetimes.

The time traces of the fluorescence intensity and spectra affirmed short- and long-lived blinking lifetimes are shown in FIGS. 11a-f Long-lived events displayed lifetimes ranging from 1 to 15 seconds (FIG. 11a), whereas short-lived events occurred in less than one second (generally tens of ms) (FIG. 11b). By monitoring the emission intensity of repetitive stochastic events, we found individual molecules have consistent blinking photon count. Spectra of both blinking events were highly dependent on sample location. However, localized events, likely from the same molecule or potentially sub-molecular structure of the long-chain polymer, displayed nearly identical spectral information regardless of the frequency and duration of the event. Nonetheless, spectra of short-lived events were characteristically blue-shifted and had narrower spectra compared with their long-lived counterparts. The observed stochastic events were sparse temporally, eliminating the possibility for long spectral integration times due to the dominant PMMA Raman signal (FIG. 11c), which may explain the lack of previous reports. Therefore, to obtain accurate spectra, high-speed video was acquired with the spectral EMCCD detector and removed the constant Raman background. Using high imaging speeds (85 fps), the Raman background was less of a factor compared with the observed stochastic blinking. Due to the measured lifetimes and broad spectral emission, we determined that the radiation was intrinsic fluorescence.

FIG. 11a is an example image representing photon counts within the one of three selected spectral bands. Band R1 contains the highest energy scattering peaks ranging from 1345 cm−1 to 1760 cm−1. FIG. 11b is an example image representing photon counts within the one of three selected spectral bands. Band C contains the background scattering ranging from 2000 cm−1 to 2470 cm−1. FIG. 11c is an example image representing photon counts within the one of three selected spectral bands. Band R2 contains the lower energy scattering peaks ranging from 2600 cm−1 to the 3000 cm−1. FIG. 11d is an example image representing corresponding intensity probability distributions of stochastic emissions for Band R1. Two different Poisson distributions can be found in Bands R1 and R2, while a single distribution is observed in Band C. FIG. 11e is an example image representing corresponding intensity probability distributions of stochastic emissions for Band C. Two different Poisson distributions can be found in Bands R1 and R2, while a single distribution is observed in Band C. FIG. 11f is an example image representing corresponding intensity probability distributions of stochastic emissions for Band R2. Two different Poisson distributions can be found in Bands R1 and R2, while a single distribution is observed in Band C.

Figure 12:
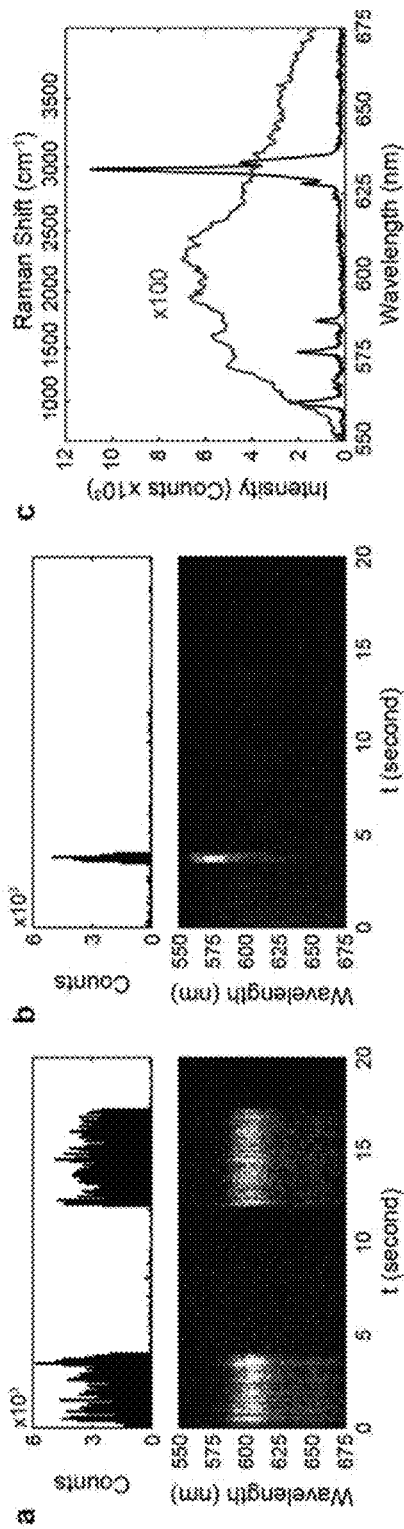
FIGS. 12a-12c show example images including stochastic emission.

FIG. 12a is an example image showing the stochastic emission from long-lived events at a single location and the respective spectra in time. The spectra and photon count were consistent for each event consecutive flashing event. FIG. 12b is an example image showing the stochastic emission from short-lived events also had consistent spectra for each location; however, they were comparatively narrower and blue-shifted in PMMA. FIG. 12c is an example image showing that for longer integration times, Raman radiation was more dominant than stochastic radiation. Therefore, to obtain accurate stochastic spectra, the stochastic emission was summed over 1,000 consecutive frames and multiplied by 100 for comparison.

Figure 13:
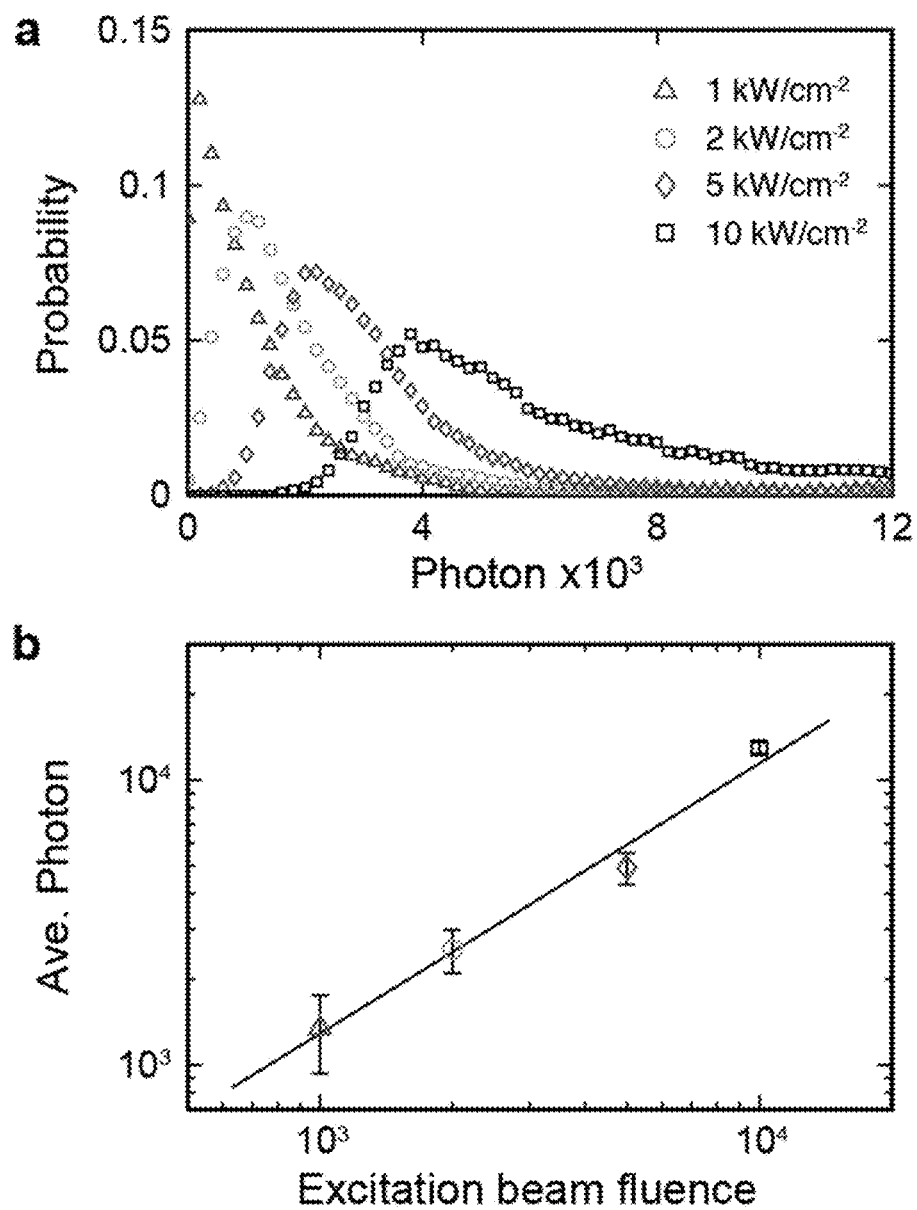
FIGS. 13a-b show the relationship between incident laser fluence and photon count of the resulting blinking events.

Intrinsic fluorescent blinking in polymers has been well studied; however, blinking from PMMA, PS, and SU-8 is a newly observed phenomenon. To confirm if the observed blinking was environmentally or photophysically induced, we varied the illuminating laser fluence (1, 2, 5, and 10 kW/cm$^2$) and measured the stochastic frequency and photon count using a second high-speed imaging EMCCD (iXon 897 Ultra, Andor). Photophysically induced changes have a linear dependence on the illuminating laser fluence, while environmentally induced changes are laser-fluence-independent. FIGS. 13a-b show the relationship between incident laser fluence and photon count of the resulting blinking events. For the power-photon count linearity order, the slope of the log-log fitting was used to determine the power relation. In our fitting (FIG. 13b), the slope was calculated to be 0.95, thus confirming the linear relation. Linear increases in incident laser fluence resulted in a higher photon count of the stochastic events and an overall linear increase in photon number, confirming that all fluorescent blinking results from photophysical changes induced by laser excitation.

Figure 14:
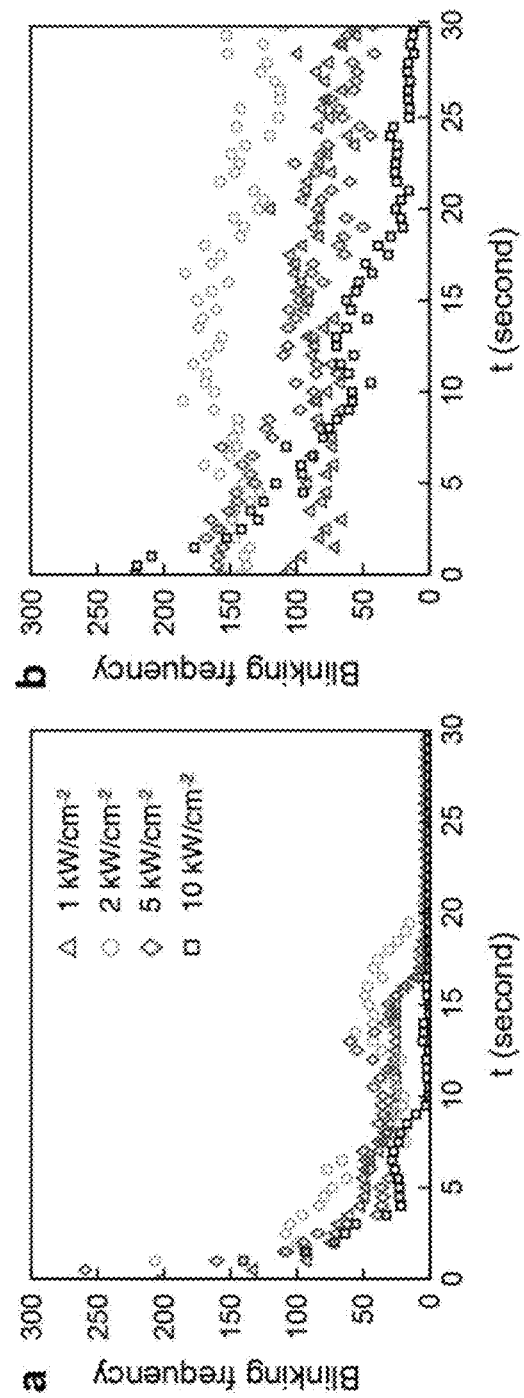
FIGS. 14a-b show example graphs showing blinking frequency with respect to illumination time.

The PMMA thin film samples displayed fast initial photobleaching. We used frame rates of 100 fps to capture the change of blinking frequency during photobleaching. Laser fluence was varied to investigate bleaching dynamics in PMMA thin film samples. For PMMA film samples tested in atmosphere, we observed photobleaching within 30 seconds of initial laser exposure for all incident fluences (FIG. 14a). As expected, the highest incident fluence induced faster photobleaching; however, bleaching occurred within 10-30 seconds for all tested fluences.

Photobleaching in the polymer matrix is often caused by oxidation diffusion, and thus we modified the PMMA film sample by covering it with deionized-water, which should reduce oxidation effects. Although the average photon count of individual stochastic events were equivalent for both immersed and non-immersed samples, the water-immersed PMMA films showed comparatively reduced photobleaching and a stable stochastic process that could be observed for at least one hour with lower beam fluences (FIG. 14b). In both circumstances, the blinking frequency and intensity stabilized after exposure for several minutes, but the frequency of events were significantly lower for non-immersed samples. Oxidation is less likely in immersed samples, allowing stable photo-emission with slower photobleaching.

Example 2

To determine the minimal resolvable feature size of our STORM setup using the intrinsic fluorescence from PMMA, the theoretically and experimentally resolution was calculated. Depending on detector parameters and filter efficiency, the theoretical resolution of STORM imaging can vary. If the probability of simultaneous stochastic light generation from multiple nearby regions is negligible, we can assume the detected PSFs to be from a single stochastic event. The center of the PSF can then be approximated with the probability equation, $$\sigma_{\mu_i} = \sqrt{\left(\frac{s_i^2}{N}\right) + \left(\frac{a^2/12}{N}\right) + \left(\frac{8\pi s_i^4 b^2}{a^2 N^2}\right)}$$

where N is the number of detected photons; $s_i$ is the standard deviation of the PSF; a is the pixel size; and b is the standard deviation of the background. As the number of detected photons determines the probabilistic center of the PSFs, resolution is limited by the photon count of the stochastic radiation, the detector background, and the efficiency of the optical setup. Using the probability equation and considering the background of the detector, our experimental resolution was calculated to be approximately 37 nm for the "NU" nanopatterned sample.

Example 3

Figure 15:
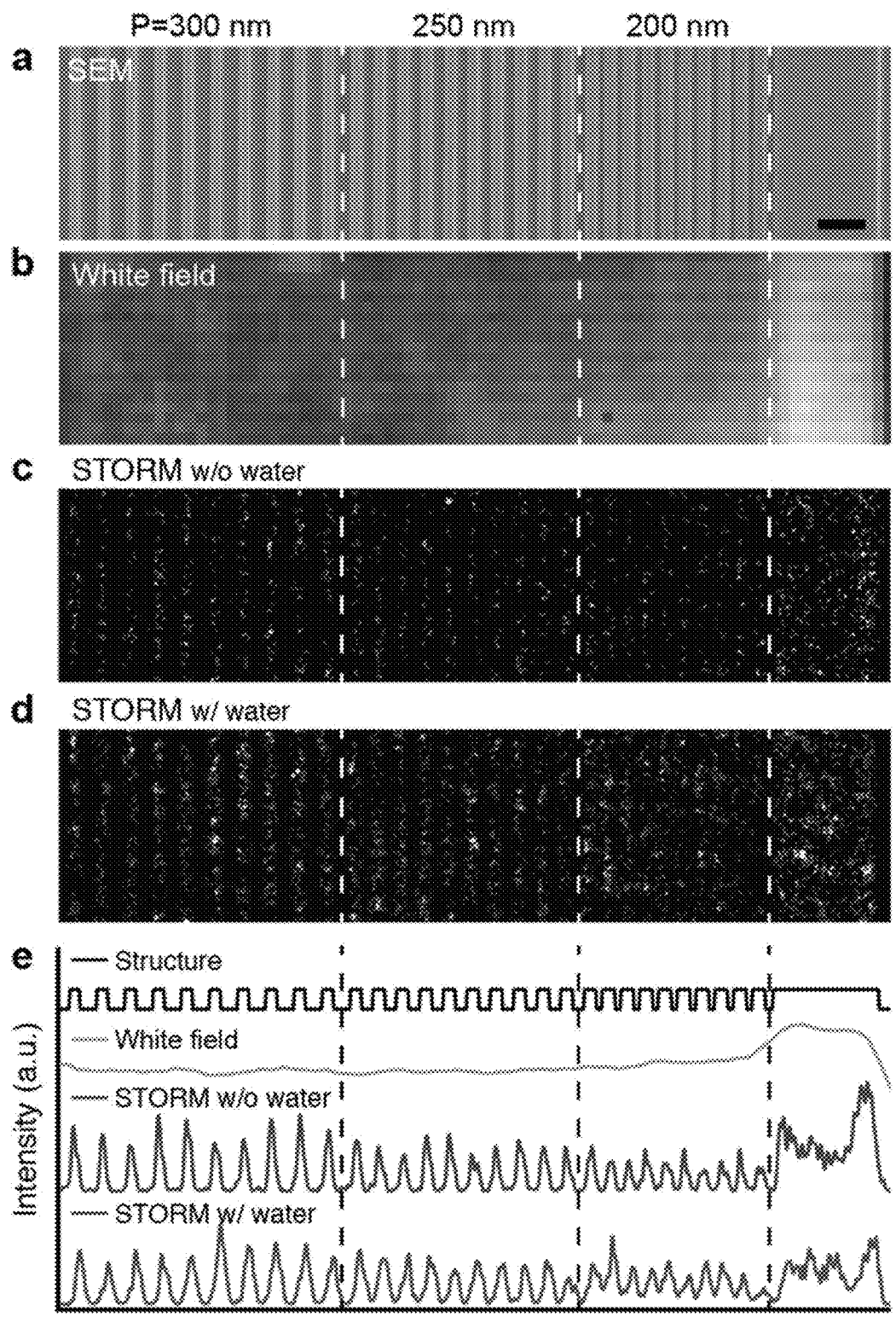
FIGS. 15a-e show an example PMMA target patterned with progressively increasing periodicity and imaged.

To experimentally verify the theoretical resolution, a new PMMA target was patterned with progressively increasing periodicity of 200 nm, 250 nm, 300 nm, and 400 nm for resolution tests (FIGS. 15a-e). SEM imaging was used to confirm periodicity and gap spacing, as shown in FIG. 15a. As expected, conventional wide-field imaging does not have the ability to resolve the line spacing of the PMMA periodic grating pattern (FIG. 15b). In order to determine the experimental resolution of intrinsic fluorescence using STORM, we collected 60,000 frames of images from both immersed and non-immersed nanostructures and performed STORM reconstruction. Conventional wide-field imaging and STORM images from non-immersed (FIG. 15c) and immersed (FIG. 15d) PMMA structures were averaged along the vertical axis to create line profiles of the intensity distribution (FIG. 15e). Clearly, patterns with periodicity of 200 nm can be well resolved for both PMMA nanopatterned samples, indicating a half-pitch resolution better than 100 nm. For immersed PMMA, a clearer image of the nanopattern was reconstructed due to the increased blinking frequency. The actual experimental resolution was better than the spacing in the nanopatterned sample. Therefore, using the ESF measured from the large PMMA bar (5 μm×1 μm), we determined the experimental resolution to be 45 nm. The experimentally quantified resolution is worse than the theoretical estimate due to small perturbations, such as fluctuations in sample position from stage drift.

Figure 16:
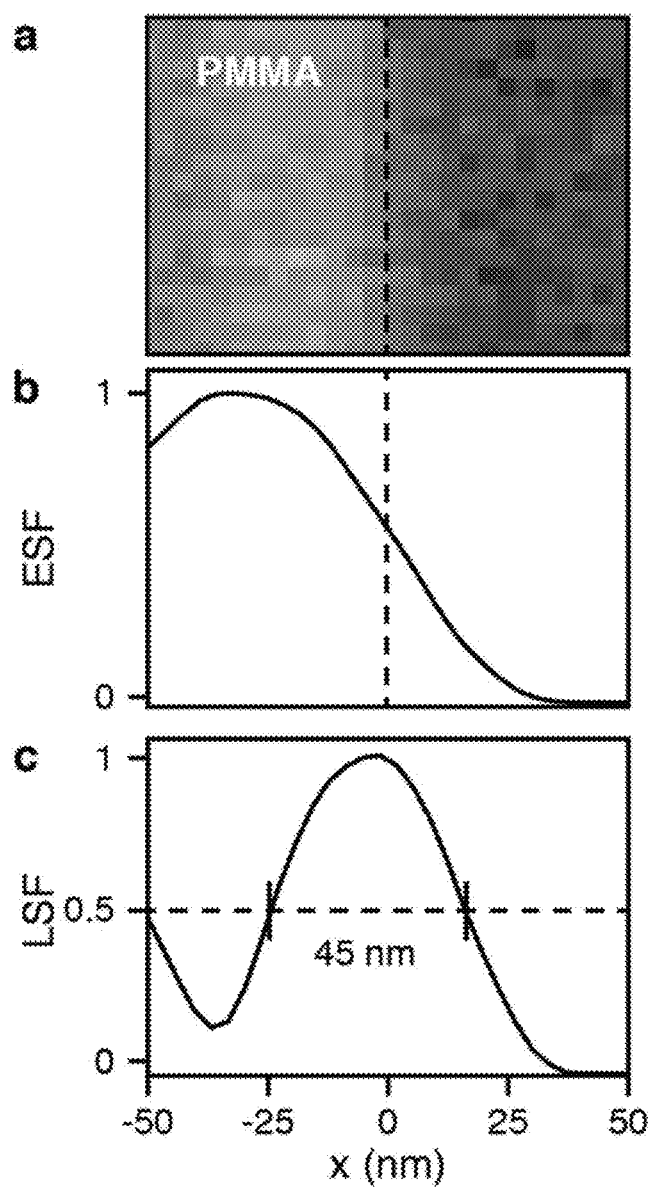
FIGS. 16a-c show example image analysis.

FIGS. 16a-c show example image analysis. FIG. 16a is an example image showing an SEM image of the edge of a solid PMMA bar used to determine lateral resolution. FIG. 16b is an example image showing an edge spread function (ESF) obtained from its spectroscopic super-resolution microscopic image. FIG. 16c is an example image showing shows the line spread function (LSF) calculated from the ESF.

Figure 17:
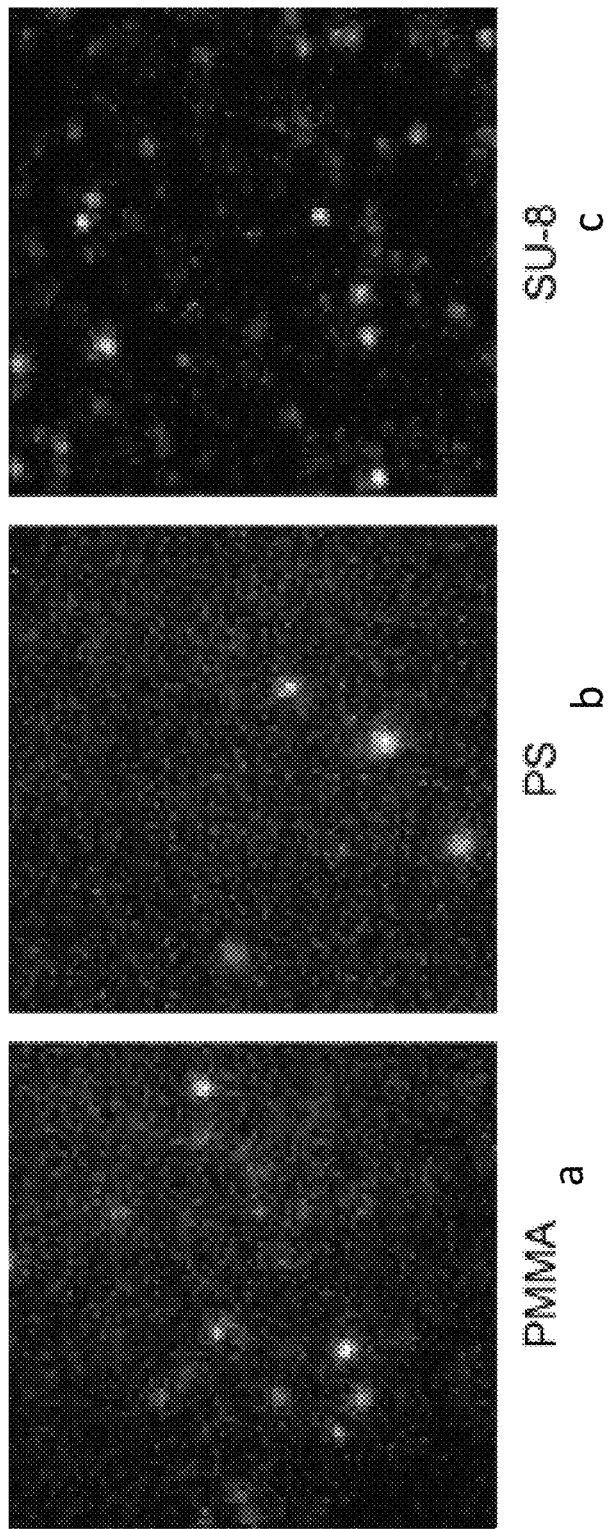
FIGS. 17a-c show example blinking events on film.

FIG. 17a is an example image of representative frames showing blinking events on PMMA films. FIG. 17b is an example image of representative frames showing blinking events on PS (polystyrene). FIG. 17c is an example image of representative frames showing blinking events on SU-8 films.

Figure 18:
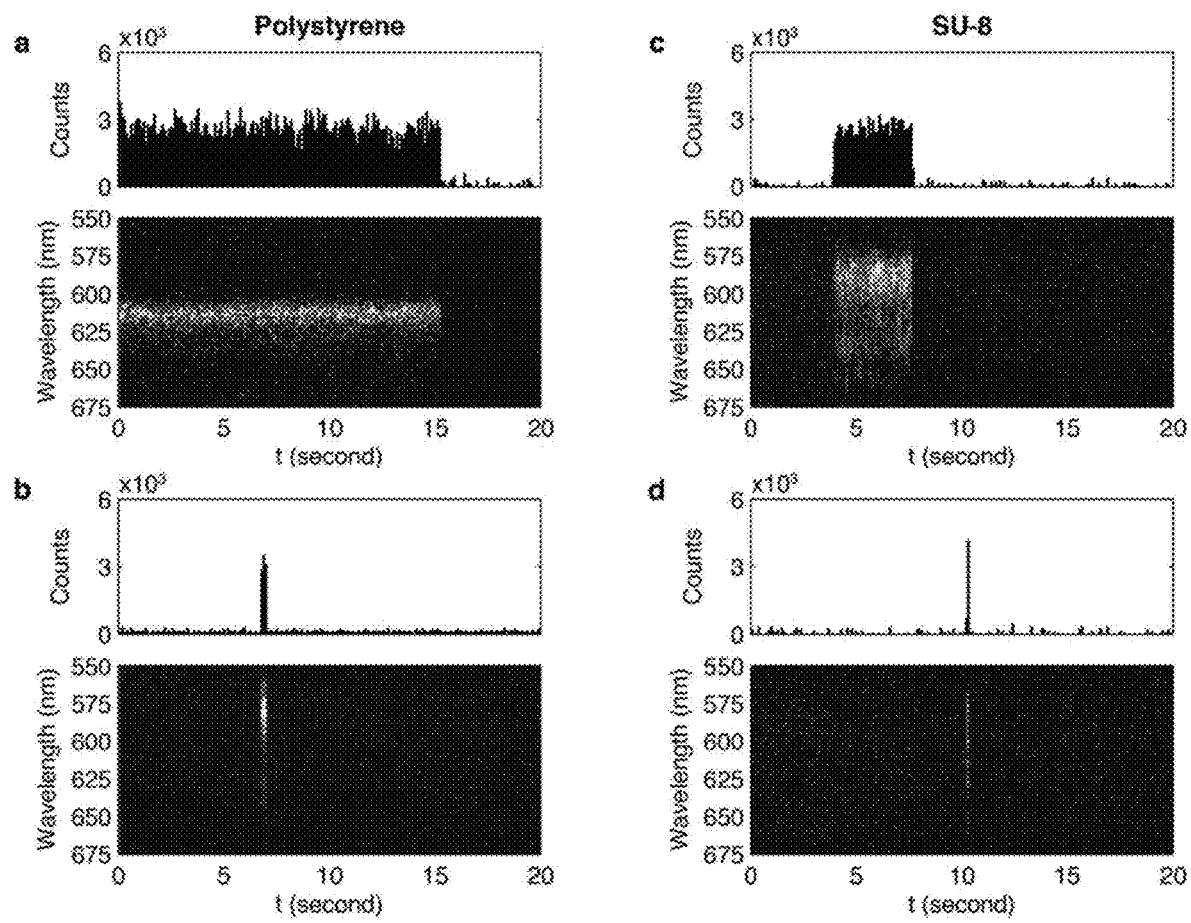
FIGS. 18a-c show example images of stochastic blinking events.

FIG. 18a is an example image showing long lived stochastic blinking events in in poly-styrene thin film samples. FIG. 18b is an example image showing short lived stochastic blinking events in in poly-styrene thin film samples. FIG. 18c is an example image showing short lived stochastic blinking events in in SU-8 thin film samples. FIG. 18d is an example image showing long lived stochastic blinking events in in SU-8 thin film samples Example 4

In certain examples, the working principle of SPLM is illustrated by replacing a diffraction limit wide field image with a time-sequence of sparsely distributed emissions. Thus, the centroid of individual emission events can be determined by the well-established localization algorithm with nanometer accuracy, which can be accumulated to construct the sub-diffraction-limited image of the sample. A modest continuous-wave laser illumination has been used to excite fluorescent molecules into long-lived dark states and subsequently recover them by stochastic photo-switching. A fluorescence image was coupled into a Czerny-Turner type monochromator for spectroscopic imaging. The collected fluorescent emission was divided at approximately a 1:3 ratio between the zero-order and first-order. A mirror was placed in the spectrometer to project the adjust the position of the zero-order image so both zero-order and first-order images can be acquired simultaneously using the same EMCCD camera. This is a critical step for establishing the necessary temporal and spatial correlations among the zero-order and first-order images in dealing with the stochastic emission events. The mirror position was carefully aligned to avoid overlapping between zero- and first-order images, while also maximizing the field of view on the EMCCD. A spectral image was obtained side-by-side to the zero-order image with a resolution of 0.63 nm/pixel. Since each stochastic localized (blinking) event can be treated as a sub-diffraction-limited point source, the high resolution spectrum can be captured using the monochromator without the need for an entrance slit. Therefore, SPLM allows simultaneous acquisition of wide field-of-view and the associated fluorescent spectra. The zero-order image was reversed due to the additional mirror, but else remained identical to images obtained using conventional PLM (without the monochromator). Thus, the centroids of individual stochastic emission obtained from the zero-order images will be used to construct super-resolution of the sample and to provide inherent reference points to determine the origin of the measured spectrum for each stochastic emission event.

The spatial and spectral resolution of the reported spectroscopic super-resolution imaging method are fundamentally limited by the number of photons being collected from each fluorescent molecule, which is ultimately determined by the irreversible photo-bleaching threshold. Additionally, the background signals, such as auto-fluorescence, Raman, and Rayleigh scattering from the sample, also need to be carefully considered in order to achieve the optimal spatial and spectral resolution. In SPLM, the zero-order image is analyzed by utilizing the standard localization algorithm (QuickPALM, ImageJ plug-in) to determine the location of individual blinking events, which is identical to the standard STORM/PALM methods. A centroid position has been used to 1) determine the location of each activated fluorescent molecule and 2) establish the reference point of the corresponding emission spectrum from the measured first-order image. The dispersion of the imaging system was calibrated prior to the image acquisition. Background signals were removed by subtracting the average of adjacent image frames without the presence of stochastic emission. Finally, the spectrum was further normalized by the wavelength dependent transmission and reflection of optical components and the camera quantum efficiency. Spectra can be shown from representative individual blinking events. Considering the sparse nature of the stochastic emission, the measured spectra from neighboring fluorescence molecules are less likely to overlap in space. In rare events, in which overlapping occurs, the spectra of neighboring fluorescence molecules can be separated with a modified spectral linear unmixing algorithm. Finally, spectroscopic super-resolution microscopic imaging can be accomplished.

Since only one fourth of the total emission was allocated to the zero-order image, the localization precision is potentially limited by the reduction of photon number, yielding a 2-fold reduction in the image spatial resolution based on Nyquist criterion. During the period of image acquisition, molecules can be repetitively activated and their emission can be sorted when there is a reasonable match in both spatial and spectral coordinates, which we hereby called spectral regression.

To characterize precision of the SPLM, we used mixed actin monomers labeled with Alexa Fluor 532 and Alexa Fluor 568, respectively. When observing a single diffraction limited spot, an individual dye molecule was repetitively activated during the period of image acquisition (20-s, 1000-frames). The measured average photons per frame is 800, corresponding to a Nyquist criterion of ~40 nm. Spectral regression was applied for nearby localizations and use an averaging procedure to further improve localization precision. For molecules that matched well with each other in both spatial and spectral coordinates, the final coordinates were determined as the average of all emitting events. The localization precision was improved from ~35 nm to ~10 nm, as indicated by the line profiles.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for imaging a target, the method comprising:
   (a). activating a subset of light-emitting molecules in a wide-field area of the target using an excitation light;
   (b). capturing one or more images of the light emitted from the subset of the molecules illuminated with the excitation light;
   (c). dividing light emitted from the subset of the molecules illuminated with the excitation light into a first light and a second light;
   (d). adjusting a position of the first light on an imager via a mirror, wherein the mirror is positioned such that the first light but not the second light is reflected by said mirror;
   (e). using the first light, localizing one or more activated light emitting molecules, using one or more single molecule microscopic methods to obtain localization information; wherein the step of localizing comprises summing the localization information from the same one or more activated light emitting molecules to improve a localization precision;
   (f). simultaneously, using the second light, capturing spectral information for the same localized activated light emitting molecules using one or more spectroscopic methods, such that the localization information is obtained and the spectral information is captured simultaneously for each of the one or more activated light emitting molecules;
   (g). resolving one or more non-diffraction limited images of the wide-field area of the target from the one or more captured images using a combination of the localization and spectral information for the localized activated light emitting molecules; and
   (h). displaying the one or more non-diffraction limited images.

2. The method of claim 1, wherein the step of activating the subset of molecules further comprises illuminating the sample with low-intensity activation light that stochastically photoswitches the subset of light-emitting particles.

3. The method of claim 1, wherein the light-emitting molecules are not extrinsically labeled.

4. The method of claim 1, wherein the light-emitting molecules comprises one or more light-emitting extrinsic labels.

5. The method of claim 4, wherein the light-emitting extrinsic label is selected from the group consisting of fluorescent tag, fluorescent protein, fluorophore, fluorescent probe, quantum dot, fluorescence resonance energy transfer probe, and diode laser excitable probe.

6. The method of claim 1, wherein the step of resolving one or more non-diffraction limited images further comprises capturing one or more zero-order images and one or more first-order spectral images simultaneously or substantially simultaneously.

7. The method of claim 1, wherein the one or more single molecule microscopic methods is selected from the group consisting of stochastic optical reconstruction microscopy, spectral precision distance microscopy (SPDM), spectral precision distance microscopy with physically modifiable fluorophores (SPDMphymod), photo activated localization microscopy (PALM), photo-activation localization microscopy (FPALM), photon localization microscopy (PLM), direct stochastical optical reconstruction microscopy (dSTORM), super-resolution optical fluctuation imaging (SOFI), and 3D light microscopical nanosizing microscopy (LIMON).

8. The method of claim 7, wherein the step of resolving one or more non-diffraction limited images further comprises determining the centroid positions of the one or more localized activated light-emitting molecules and establishing a reference point of the corresponding emission spectrum of one or more localized activated light-emitting molecules.

9. The method of claim 1, wherein the step of resolving one or more non-diffraction limited images further comprises resolving individual spectral curves with a spectral linear unmixing algorithm and analysis by spectral regression.

10. The method of claim 1, wherein the step of resolving one or more non-diffraction limited images further comprises normalizing spectra.

11. The method of claim 1, wherein the emission spectra from the same activated light-emitting molecule are classified by spectral regression.

12. The method of claim 1, wherein the one or more spectroscopic methods is selected from the group consisting of Raman spectroscopy, optical fluorescence microscopy, infrared spectroscopy, ultraviolet spectroscopy, laser microscopy and confocal microscopy.

13. The method of claim 1, wherein the step of activating a subset of light-emitting molecules in the wide-field area of the target and the step of capturing one or more images of the light emitted from the subset of the particles illuminated with excitation light is performed with one or more light wavelengths selected outside of the primary absorption-emission bands of the target.

14. The method of claim 1, wherein the target is selected from the group consisting of polymer, protein, nucleic acid, lipid, carbohydrate, cell, cells, subcellular organelles, subcellular structures, extracellular structures, nanofabricated structures, nanoparticles, nanostructures, semiconductor chips, and crystals.

15. The method of claim 1, wherein the step of resolving one or more non-diffraction limited images further comprises applying an agent to the target that reduces photobleaching.

16. The method of claim 1, wherein the step of resolving one or more non-diffraction limited images is performed in three dimensions (3D).

17. The method of claim 1, wherein the step of resolving one or more non-diffraction limited images further comprises summing the resolved images.

18. The method of claim 1, wherein the step of capturing one or more images of the light emitted from the subset of the particles illuminated with excitation light is performed using intrinsic contrast of the target.

19. The method of claim 1, wherein the step of displaying the one or more non-diffraction limited images is used to detect a feature of the target selected from the group consisting of structural feature, chemical feature, structural defect, chemical defect, target quality, disease, disease state, target sequence and target composition.

20. The method of claim 1, wherein the step of resolving one or more non-diffraction limited images is performed with an imaging resolution less than 100 nm.

21. A system for imaging a target, the system comprising:
   (a). one or more light sources configured to activate a subset of light-emitting molecules, in a wide field area of the target;
   (b). a microscope feature configured to capture optical images of the subset of light-emitting molecules in the wide field area of the target;
   (c). a spectrometer configured to simultaneously capture spectral information for individual light-emitting molecules in the subset of light-emitting molecules in the wide field area of the target while localizing the one or more activated light emitting molecules to obtain localization information; such that the localization information is obtained and the spectral information is captured simultaneously for each of the activated light emitting molecules;
   (d). a spectral filtering element;
   (e). one or more imagers configured to process the optical images, localization information, and spectral information for light-emitting molecules in the wide field area of the target to generate one or more non-diffraction limited images of the wide field area;
   (f). a display for one or more non-diffraction limited images of the wide field area;
   wherein the system is configured to divide light emitted from the subset of the molecules illuminated with the excitation light into a first light and a second light; wherein the first light is used for localizing the one or more activated light emitting molecules to obtain the localization information; wherein the second light is used to capture the spectral information; wherein the system is configured to summing the localization information from the same activated light emitting molecules to improve a localization precision of the system; and
   (g). a mirror to adjust a position of the first light on the one or more imagers, wherein the mirror is positioned such that the first light but not the second light is reflected by said mirror.

22. The system of claim 21, wherein the one or more light sources are selected from the group consisting of laser, laser diode, visible light source, ultraviolet light source and infrared light source.

23. The system of claim 21, wherein microscope is configured to localize light-emitting molecules in the wide field area of the target.

24. The system of claim 23, wherein localization is performed using a stochastic optical reconstruction localization algorithm.

25. The system of claim 21, wherein the microscope feature is configured for optical fluorescence microscopy, infrared spectroscopy, ultraviolet spectroscopy, laser microscopy and confocal microscopy.

26. The system of claim 21, wherein the spectrometer is configured for optical fluorescence microscopy, infrared spectroscopy, ultraviolet spectroscopy, laser microscopy and confocal microscopy.

27. The system of claim 21, wherein the spectral filtering element is selected from the group consisting of dispersive element, transmission grating, grating and band pass filter.

28. The system of claim 21, wherein the one or more imagers is selected from the group consisting of charged coupled device, electron multiplying charged coupled device, camera, and complementary metal-oxide-semiconductor imager.

29. The method of claim 1, wherein the localization precision is: (i) less than 40 nm based on a Nyquist criterion, (ii) selected from the range of 40 nm to 10 nm based on a Nyquist criterion, or (iii) 10 nm based on a Nyquist criterion.

30. The method of claim 1, wherein the step of dividing comprises a ratio of the first light to the second light, the ratio being 1:3.

31. The method of claim 1, wherein light emitted from the subset of the molecules in the wide-field area is not confined or masked by one or more slits or apertures; and wherein the step of activing comprises illuminating the wide-field area without use of laser line scanning, laser spot scanning, imaging through one or more moving slits or hyperspectral imaging through the use of filters.

32. The method of claim 1, wherein the localization information is obtained and the spectral information is captured simultaneously using said imager.

33. The method of claim 1, wherein the spectral information is characterized by a spectral resolution of 0.63 nm.

* * * * *